United States Patent
Keillor et al.

(10) Patent No.: US 8,835,641 B2
(45) Date of Patent: Sep. 16, 2014

(54) FLUORESCENT MARKERS AND USE THEREOF FOR LABELING SPECIFIC PROTEIN TARGETS

(75) Inventors: Jeffrey Keillor, Montreal (CA); Karine Caron, Montreal (CA)

(73) Assignee: University of Ottawa, Ottawa (CA)

( * ) Notice: Subject to any disclaimer, the term of this patent is extended or adjusted under 35 U.S.C. 154(b) by 0 days.

(21) Appl. No.: 13/185,656

(22) Filed: Jul. 19, 2011

(65) Prior Publication Data

US 2012/0171665 A1 Jul. 5, 2012

Related U.S. Application Data

(60) Provisional application No. 61/365,389, filed on Jul. 19, 2010.

(51) Int. Cl.
*C07D 401/14* (2006.01)
*C07D 207/452* (2006.01)
*C07D 405/14* (2006.01)
*C07F 5/02* (2006.01)
*G01N 21/64* (2006.01)

(52) U.S. Cl.
CPC .......... *C07D 207/452* (2013.01); *C07D 401/14* (2013.01); *C07D 405/14* (2013.01); *G01N 2021/6439* (2013.01); *C07F 5/022* (2013.01)
USPC ........................................ 546/278.7; 436/92

(58) Field of Classification Search
CPC .................................................... C07D 401/14
USPC ........................................ 546/278.7; 436/92
See application file for complete search history.

(56) References Cited

U.S. PATENT DOCUMENTS

| | | | |
|---|---|---|---|
| 7,700,375 B2 | 4/2010 | Keillor et al. | |
| 2004/0171014 A1* | 9/2004 | Smith | 435/6 |
| 2006/0147948 A1* | 7/2006 | Keillor et al. | 435/6 |

OTHER PUBLICATIONS

Girouard et al. (J. Am. Chem. Soc. 2005, 127, 559-566).*
Liang, F. et al. "Gene index analysis of the human genome estimates approximately 120,000." Nat. Genet. 2000, 25, 239-240.
Roest Crollius, H. et al. "Estimate of human gene number provided by genome-wide analysis using." Nat. Genet. 2000, 25, 235-238.
Ewing, B. et al. "Analysis of expressed sequence tags indicates 35,000 human genes." Nat. Genet. 2000, 25, 232-234.
Haughland, R. P. "Handbook of Fluorescent Probes and Research Chemicals." Molecular Probes. Eugene. Oreg. 1992, 5th Edn.
Sipple, T. O. "New fluorochromes for thiols: maleimide and iodoacetamide derivatives of 3-phenyl coumarin fluorophore." J. Histochem. Cytochem. 1981, 29, 314-316.
Corrie, J. E. T. "Thiol-reactive Fluorescent Probes for Protein Labelling." J. Chem. Soc. Perkin Trans. 1, 1994, 2975-2982.
Zhang, J. et al. "Creating New Fluorescent Probes for Cell Biology." Nature Rev. 2002, 3, 906-918.
Tsien, R. Y. "The Green Fluorescent Protein." Annu. Rev. Biochem. 1998, 67, 509-544.
Griffin, B. A. et al. "Specific Covalent Labeling of Recombinant Protein Molecules Inside Live Cells." Science 1998, 281, 269-272.
Griffin, B. A. et al. "Fluorescent labeling of recombinant proteins in living cells with FlAsH." Methods Enzymol. 2000, 327, 565-578.
Gaietta, G. et al. "Multicolor and Electron Microscopic Imaging of Connexin Trafficking." Science 2002, 296, 503-507.

(Continued)

*Primary Examiner* — Robert Havlin

(57) ABSTRACT

Novel fluorescent markers of Formula I:

Formula I

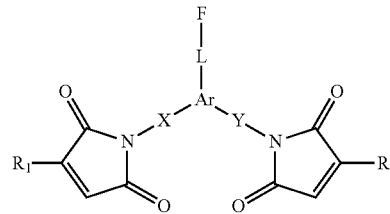

are disclosed herein, wherein X and Y are independently or together absent or are independently selected from

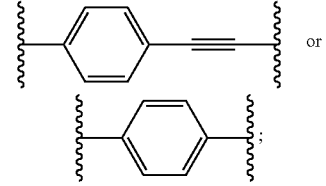

R and $R_1$ are independently selected from H and alkyl; Ar is phenyl or heteroaryl; L is absent or a spacer selected from the group consisting of —NH—; —$(CH_2)_n$NH—; —$NHSO_2$—; —$(CH_2)_n$NHCO—; -(cycloalkyl)NHCO—; —$(CH_2)_n$NHSO_2$—; -(cycloalkyl)$NHSO_2$—; —$CONH(CH_2)_n$NHCO—; —CONH(cycloalkyl)NHCO—; —$NHCO(CH_2)_n$NHCO—; —NHCO(cycloalkyl)NHCO—; —$(CH_2)_n$SO_2NH$—; -(cycloalkyl)$SO_2NH$—; —$(CH_2)_n$NHCSNH—; -(cycloalkyl)NHCSNH—; —CR=$CR_1$—; —C≡C—; —$(CH_2)_n$N=CH—; -(cycloalkyl)N=CH—; —N=CH$(CH_2)$—; —N=CH(cycloalkyl)-;

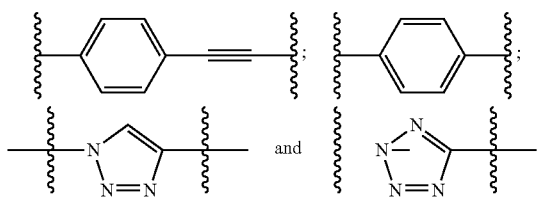

n is an integer ranging from 1 to 5; F is a fluorophore selected from the group consisting of fluorescein, rhodamine, eosin, thionine, safranin, coumarin, methoxycoumarin, dansyl, BODIPY and BODIPY derivatives; and wherein X, Y and L may be positioned in a 1,3,5; 1,2,3; 1,3,4 or in a 3,4,5 configuration respectively.

7 Claims, 8 Drawing Sheets

(56) References Cited

OTHER PUBLICATIONS

Girouard, S. et al. "Elaboration d'un fluorophore permettant une étude d'apposition protéique." M. Sc. Thesis. Université de Montréal. 2000.

Houle, M. H. et al. "Synthèse d'un composé fluorogénique permettant l'étude de l'apposition protéique." M. Sc. Thesis. Université de Montréal. 2003.

Kanaoka, Y. et al. "Studies on Protein-Sulfuryl Reagent. Synthesis of Benzimidazole Derivatives of Maleimide. Fluorescent Labeling of Maleimide." Chem. Pharm. Bull. 1964, 12, 127-134.

Guy, J. et al. "Convergent Preparation and Photophysical Characterization of Dimaleimide Dansyl Fluorogens: Elucidation of the Maleimide Fluorescence Quenching Mechanism." J. Am. Chem. Soc. 2007, 129, 11969-11977.

Langmuir, M. E. et al. "New Naphtopyranone Based Fluorescent Thiol Probes." Tetrahedron Lett. 1995, 36, 3989-3992.

Yang, J. R. et al. "Synthesis and Properties of a Maleimide Fluorescent Thiol Reagent Derived a Naphtopyranone." J. Heterocyclic Chem. 1991, 28, 1177.

Russo, A. et al. "Detection and quantitation of biological sulfhydryls." Methods Biochem. Anal. 1988, 33, 165-241.

\* cited by examiner

FLUORESCENT MARKERS AND USE THEREOF FOR LABELING SPECIFIC PROTEIN TARGETS

This application claims priority to U.S. Provisional Application No. 61/365,389 filed on Jul. 19, 2010, the entire disclosures of which are specifically incorporated herein by reference in their entirety without disclaimer.

FIELD

The present disclosure broadly relates to novel fluorescent markers. More specifically, but not exclusively, the present disclosure relates to fluorescent markers comprising a dimaleimide core connected to a fluorophore and to a process for the preparation of such fluorescent markers. Moreover, the present disclosure also relates to the use of such fluorescent markers for the labeling and detection of specific proteins targets.

BACKGROUND

The sequencing of the human genome has allowed the identification of a vast number of putative genes [1, 2, 3]. However, the function of only a small number of these genes can be inferred from their primary sequences. New techniques and agents are needed to cope with the task of assigning functional roles to these gene products. This implies determination of how, when and where they are involved in specific biochemical pathways. Ideally, these techniques and agents will allow the rapid screening of substantial subsets of the sum of a genome's products.

Although many proteins have been identified by functional cloning of novel genes, this "expression cloning" approach remains a significant experimental challenge. Certain proteomic methods have been designed for broad and rapid screening, but they are largely limited to in vitro application and do not necessarily provide information pertinent to living cells. Moreover, although these methods can verify what genes are expressed, it is even more important to understand the dynamic patterns of in vivo protein expression and localization. For this, more powerful methods of detection of specific proteins and their interactions inside living cells are urgently required.

Several labeling techniques have been developed that involve the use of fluorescent dyes bearing reactive functional groups such as succinimidyl esters or maleimides, known to react with amines or thiols [4, 5, 6]. Although these techniques are typically non-specific—many such functional groups exposed on the surface of any protein may be labeled—the characterization of these small molecule fluorophores teaches us the general requirements for solubility and cell permeability. However, in the proteomic context, they do not provide a general means for gathering information on specific protein targets.

The genetic fusion of target proteins to fluorescent proteins such as jellyfish green fluorescent protein (GFP) is another technique that has seen broad application [7]. However, there are some serious limitations to this method. For example, the entire sequence of GFP must be properly folded into its 11-stranded β-barrel structure for it to function as a fluorophore, but it folds very slowly and is prone to aggregation. Moreover, GFP fluorescence suffers from low quantum yields, is sensitive to the environment of its fusion with test proteins and is also difficult to distinguish from the autofluorescent background of living cells. Furthermore, the steric bulk of a 27 kDa β-barrel protein can significantly perturb the interactions of the test proteins [7, 8]. In summary, the use of GFP derivatives can be inefficient and intrusive.

The use of certain small organometallic molecules capable of reacting specifically with four cysteine residues has been previously illustrated [9, 10, 11]. These cysteine residues were arranged in what was originally thought to be an α-helical conformation, but it was later shown that a β-turn conformation was optimal for their reaction with the fluorogenic arsenate compounds employed. In the application of this method, the fusion of a small probe protein of appropriate sequence to the target test protein allows it to be fluorescently labeled in live cells. Although these metallic complexes may not be broadly applicable to in vivo protein labeling studies due to their acute toxicity, they nevertheless demonstrate the feasibility of the use of small molecules to react preferentially with multiple thiol groups on a protein scaffold even in live cells, in the presence of several equivalents of simple native thiols. Furthermore, these small molecules illustrate the possibility of specific labeling of a test protein expressed as a fusion protein with a target sequence comprising an appropriate protein conformational motif.

A rational design strategy in which de novo minimal peptides of less than 30 amino acids react with novel synthetic probe reagents that fluoresce only after their reaction with the minimal folded peptides, have been previously described [12, 13].

Maleimide groups have long been used in applications that exploit their propensity to react selectively with thiol groups, undergoing Michael addition reactions through their C2=C3 double bond [14]. Maleimides are also known to quench fluorescence, probably due to their participation in a photo-induced electron transfer (PET), allowing non-radiative relaxation of the fluorophore's excited state. The thiol addition reaction breaks the conjugation of the maleimide group, altering the energy levels of its molecular orbitals and removing its capacity to quench fluorescence [15]. These properties were demonstrated recently in the characterization of a naphthopyranone derivative bearing a maleimide group whose fluorescence increased dramatically upon reaction with glutathione [16, 17].

Compounds bearing two maleimide groups attached directly to fluorescent cores whose latent fluorescence is quenched when their maleimide groups undergo a specific thiol addition reaction have been previously described by Keillor et al. [18]. The labeling process required designing complementary α-helical proteins bearing two cysteine residues appropriately positioned to react with the fluorogens. Genetically fusing the helical probe peptides to proteins of interest provides for selectively labeling the target sequence in living cells with the fluorogenic molecules.

The present disclosure refers to a number of documents, the content of which is herein incorporated by reference in their entirety.

SUMMARY

The present disclosure broadly relates to novel fluorescent markers comprising a dimaleimide core connected to a fluorophore and to a process for the preparation of such fluorescent markers.

As broadly claimed, the present disclosure relates to a fluorescent marker of Formula I:

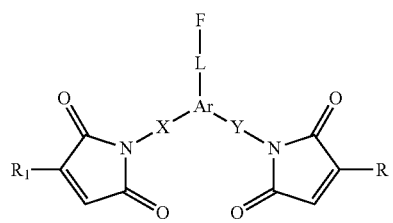

Formula I wherein:

X and Y are independently or together absent or are independently selected from

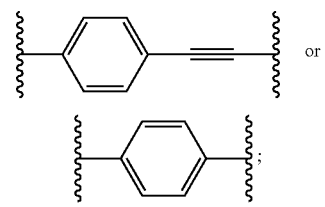

or

R and R₁ are independently selected from H and alkyl;

Ar is aryl or heteroaryl;

L is absent or a spacer selected from the group consisting of —NH—; —(CH₂)ₙNH—; —NHSO₂—; —(CH₂)ₙNHCO—; -(cycloalkyl)NHCO—; —(CH₂)ₙNHSO₂—; -(cycloalkyl)NHSO₂—; —CONH(CH₂)ₙNHCO—; —CONH(cycloalkyl)NHCO—; —NHCO(CH₂)ₙNHCO—; —NHCO(cycloalkyl)NHCO—; —(CH₂)ₙSO₂NH—; -(cycloalkyl)SO₂NH—; —(CH₂)ₙNHCSNH—; -(cycloalkyl)NHCSNH—; —CR=CR₁—; —C≡C—; —(CH₂)ₙN=CH—; -(cycloalkyl)N=CH—; —N=CH(CH₂)—; —N=CH(cycloalkyl)-;

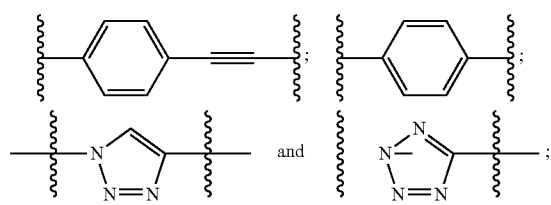

n is an integer ranging from 1 to 5;

F is a fluorophore selected from the group consisting of fluorescein, rhodamine, eosin, thionine, safranin, coumarin, methoxycoumarin, dansyl, BODIPY; and BODIPY derivatives; and wherein X, Y and L may be positioned in a 1,3,5; 1,2,3; 1,3,4 or in a 3,4,5 configuration respectively.

In an embodiment, the present disclosure relates to a molecule of Formula Ia:

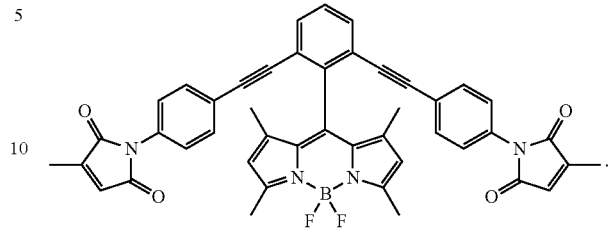

Formula Ia

In an embodiment, the present disclosure relates to a molecule of Formula Ib:

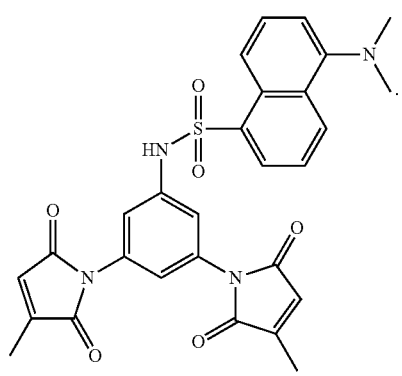

Formula Ib

In an embodiment, the present disclosure relates to a molecule of Formula Ic:

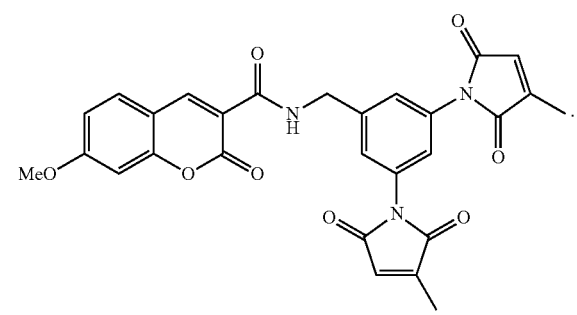

Formula Ic

In an embodiment, the present disclosure relates to a molecule of Formula Id:

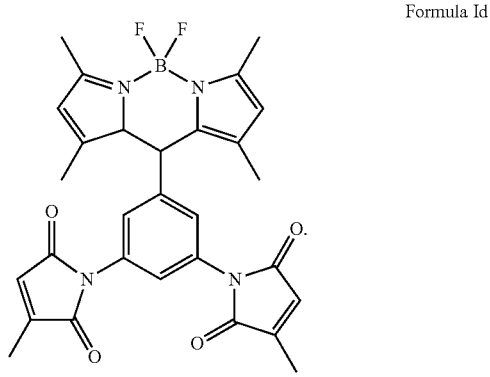

Formula Id

In an embodiment, the present disclosure relates to a molecule of Formula Ie:

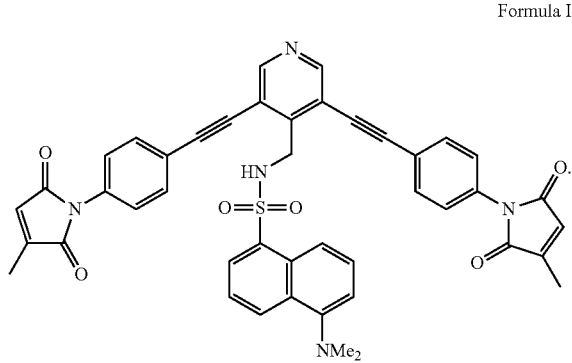

Formula Ie

In an embodiment, the present disclosure relates to a method for detecting target proteins having sterically unhindered sulfhydryl groups, the method comprising:

providing a fluorescent marker of Formula I:

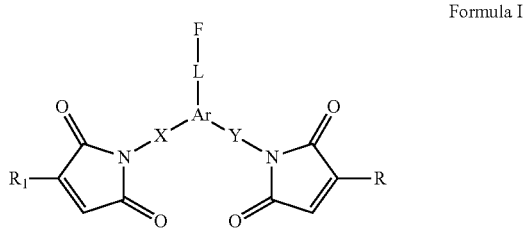

Formula I wherein:

X and Y are independently or together absent or are independently selected from

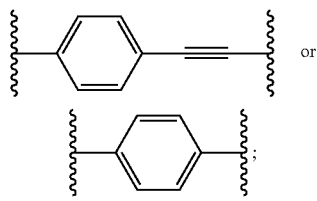

R and $R_1$ are independently selected from H and alkyl;

Ar is phenyl or heteroaryl;

L is absent or a spacer selected from the group consisting of —NH—; —$(CH_2)_n$NH—; —$NHSO_2$—; —$(CH_2)_n$NHCO—; -(cycloalkyl)NHCO—; —$(CH_2)_n$$NHSO_2$—; -(cycloalkyl)$NHSO_2$—; —$CONH(CH_2)_n$NHCO—; —CONH(cycloalkyl)NHCO—; —$NHCO(CH_2)_n$NHCO—; —NHCO(cycloalkyl)NHCO—; —$(CH_2)_n$$SO_2$NH—; -(cycloalkyl)$SO_2$NH—; —$(CH_2)_n$NHCSNH—; -(cycloalkyl)NHCSNH—; —CR=$CR_1$—; —C≡C—; —$(CH_2)_n$N=CH—; -(cycloalkyl)N=CH—; —N=CH$(CH_2)$—; —N=CH(cycloalkyl)-;

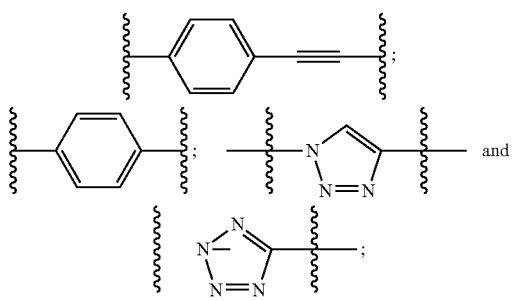

n is an integer ranging from 1 to 5;

F is a fluorophore selected from the group consisting of fluorescein, rhodamine, eosin, thionine, safranin, coumarin, methoxycoumarin, dansyl, BODIPY and BODIPY derivatives; and wherein X, Y and L may be positioned in a 1,3,5; 1,2,3; 1,3,4 or in a 3,4,5 configuration respectively;

providing at least a target protein having sterically unhindered sulfhydryl groups, or a target protein linked or fused to a protein of interest; or providing nucleic acid molecules that code for the target protein or a target protein fused to a protein of interest as defined in b) and subsequently allowing the nucleic acid molecules to produce their coded products;

allowing reaction of the target protein having sterically unhindered sulfhydryl groups or a target protein fused to a protein of interest with the fluorescent marker to generate a fluorogen adduct; and detecting a fluorescent signal from the fluorogen adduct.

In an embodiment, the present disclosure relates to a method for detecting biomolecular interactions between a first interacting protein and a second interacting protein, wherein the first interacting protein is linked or fused to a first target protein having sterically unhindered sulfhydryl groups, and the second interacting protein is linked or fused to a second target protein having sterically unhindered sulfhydryl groups, the method comprising:

providing a fluorescent marker of Formula I:

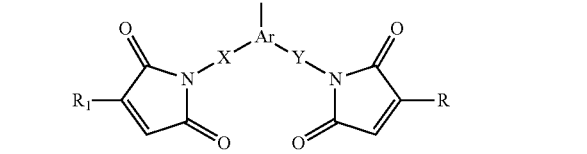

Formula I wherein:

X and Y are independently or together absent or are independently selected from

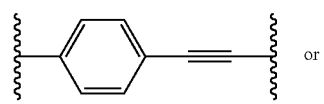

-continued

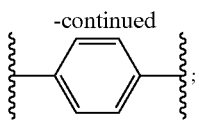

R and $R_1$ are independently selected from H and alkyl;

Ar is phenyl or heteroaryl;

L is absent or a spacer selected from the group consisting of —NH—; —$(CH_2)_n$NH—; —$NHSO_2$—; —$(CH_2)_n$NHCO—; -(cycloalkyl)NHCO—; —$(CH_2)_n$$NHSO_2$—; -(cycloalkyl)$NHSO_2$—; —CONH$(CH_2)_n$NHCO—; —CONH(cycloalkyl)NHCO—; —NHCO$(CH_2)_n$NHCO—; —NHCO(cycloalkyl)NHCO—; —$(CH_2)_n$$SO_2$NH—; -(cycloalkyl)$SO_2$NH—; —$(CH_2)_n$NHCSNH—; -(cycloalkyl)NHCSNH—; —CR=$CR_1$—; —C≡C—; —$(CH_2)_n$N=CH—; -(cycloalkyl)N=CH—; —N=CH$(CH_2)$—; —N=CH(cycloalkyl)-;

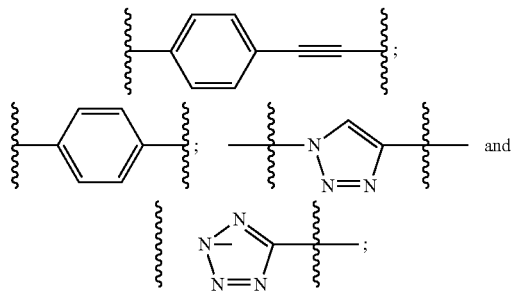

n is an integer ranging from 1 to 5;

F is a fluorophore selected from the group consisting of fluorescein, rhodamine, eosin, thionine, safranin, coumarin, methoxycoumarin, dansyl, BODIPY and BODIPY derivatives; and wherein X, Y and L may be positioned in a 1,3,5; 1,2,3; 1,3,4 or in a 3,4,5 configuration respectively;

providing at least a first target protein having sterically unhindered sulfhydryl groups linked or fused to the first interacting protein; or providing nucleic acid molecules that code for the first target protein or the first target protein fused to the first interacting protein as defined in b) and subsequently allowing the nucleic acid molecules to produce their coded products;

allowing reaction of the first target protein having sterically unhindered sulfhydryl groups linked or fused to the first interacting protein with the fluorescent marker to generate a fluorogen adduct;

providing at least a second fluorescent marker as defined in step a);

providing at least a second target protein having sterically unhindered sulfhydryl groups linked or fused to the second interacting protein, or providing nucleic acid molecules that code for the second target protein or the second target protein fused to the second interacting protein as defined in e) and subsequently allowing the nucleic acid molecules to produce their coded products;

allowing reaction of the second target protein having sterically unhindered sulfhydryl groups linked or fused to the second interacting protein with the fluorescent marker to generate a second fluorogen adduct;

allowing association of the first and second fluorogen adducts through the interaction of the first and second target proteins having sterically unhindered sulfhydryl groups linked or fused to the first and second interacting proteins to form a complex; and detecting a fluorescent signal from the complex of target proteins having sterically unhindered sulfhydryl groups, interacting proteins and fluorescent markers.

In an embodiment, the present disclosure relates to a kit for assaying target proteins having sterically unhindered sulfhydryl groups, the kit comprising a fluorescent marker of Formula I.

In an embodiment, the present disclosure relates to a kit for assaying biomolecular interactions between a first interacting protein and a second interacting protein, wherein the first interacting protein is linked or fused to a first target protein having sterically unhindered sulfhydryl groups, and the second interacting protein is linked or fused to a second target protein having sterically unhindered sulfhydryl groups, the kit comprising at least two fluorescent markers of Formula I.

In an embodiment the present disclosure relates to a fluorescent protein labeling assay comprising a fluorogen and an appropriate protein probe or probes. In a further embodiment of the present disclosure, the assays are used to label target fusion proteins in vitro and in vivo.

In an embodiment, the present disclosure relates to the specific labeling of at least two different target proteins using two different fluorogens permitting the detection of their interaction through a FRET-based fluorescent assay.

In an embodiment, the present disclosure relates to a method for labeling proteins using fluorogens. In a further embodiment of the present disclosure, the fluorogens used for labeling require no other molecules to detect their fluorescence and are not toxic to living cells.

In an embodiment, the present disclosure relates to a method for detecting target proteins having sterically unhindered sulfhydryl groups, the method comprising: 1) generating a dimaleimide containing fluorogen conferring complementarity for reaction of both maleimide groups of the fluorogen with the sulfhydryl groups of the target protein having sterically unhindered sulfhydryl groups; 2) providing at least a target protein having sterically unhindered sulfhydryl groups, or a target protein linked or fused to a protein of interest; or 3) providing nucleic acid molecules that code for the target protein or a target protein fused to a protein of interest as defined in 2) and subsequently allowing the nucleic acid molecules to produce their coded products; (A) allowing reaction of the target protein having sterically unhindered sulfhydryl groups or a target protein fused to a protein of interest with the dimaleimide containing fluorogen to generate a fluorogen adduct; and (B) detecting a fluorescent signal from the fluorogen adduct.

In an embodiment, the present disclosure relates to a method for detecting biomolecular interactions between a first interacting protein and a second interacting protein, wherein the first interacting protein is linked or fused to a first target protein having sterically unhindered sulfhydryl groups, and the second interacting protein is linked or fused to a second target protein having sterically unhindered sulfhydryl groups, the method comprising: 1) generating a dimaleimide containing fluorogen conferring complementarity for reaction of both maleimide groups of the fluorogen with the sulfhydryl groups of the target proteins having sterically unhindered sulfhydryl groups; 2) providing at least a first target protein having sterically unhindered sulfhydryl groups linked or fused to the first interacting protein; or 3) providing nucleic acid molecules that code for the first target protein or the first target protein fused to the first interacting protein as defined in 2) and subsequently allowing the nucleic acid molecules to produce their coded products; (A) allowing reaction of the first target protein having sterically unhindered sulfhydryl groups linked or fused to the first interacting protein with the dimaleimide containing fluorogen to generate a fluorogen adduct; (B) generating 4) at least a second dimaleimide containing fluorogen conferring complementarity for reaction of both maleimide groups of the fluorogen with the sulfhydryl groups of the target proteins having sterically unhindered sulfhydryl groups; and 5) at least a second target protein having sterically unhindered sulfhydryl groups linked or fused to the second interacting protein, or 6) providing nucleic acid molecules that code for the second target protein or the second target protein fused to the second interacting protein as defined in 5) and subsequently allowing the nucleic acid molecules to produce their coded products; C) allowing association of the first and second dimaleimide molecules through the interaction of the first and second target proteins having sterically unhindered sulfhydryl groups linked or fused to the first and second interacting proteins to form a complex; and (D) detecting a fluorescent signal from the complex of target proteins having sterically unhindered sulfhydryl groups, interacting proteins and dimaleimide molecules.

In an embodiment, the present disclosure relates to a method for labeling multiple proteins using small molecule labeling agents.

In an embodiment, the present disclosure relates to a method for detecting the dynamics of protein localization and turnover as well as protein-small molecule, protein-protein, protein nucleic acid and protein-carbohydrate interactions.

In an embodiment, the present disclosure relates to a method for screening small molecules and small interfering RNAs.

In an embodiment, the present disclosure relates to a use of the fluorescent markers in a method for genomic screening of molecular interactions.

The foregoing and other objects, advantages and features of the present disclosure will become more apparent upon reading of the following non-restrictive description of illustrative embodiments thereof, given by way of example only.

DETAILED DESCRIPTION

Figure 1:
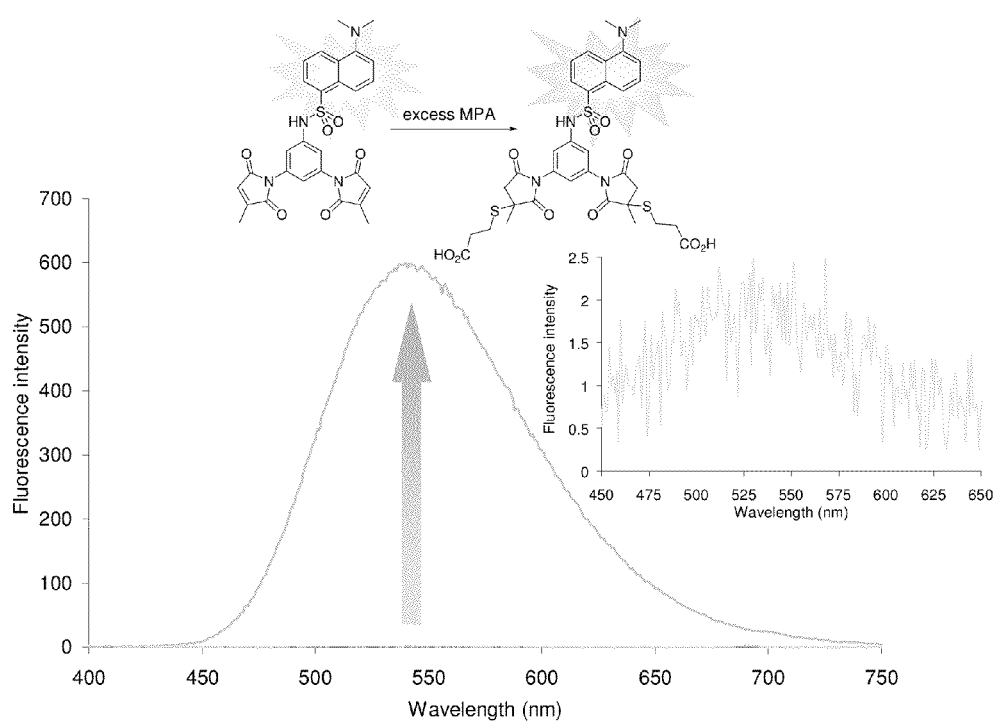
FIG. 1 is an illustration of the fluorescence enhancement ratio (FE) of fluorogen 5 when reacted with excess MPA ($\lambda_{ex}$=350 nm, DMSO)

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "alkyl" can be straight-chain or branched. Examples of alkyl residues containing from 1 to 6 carbon atoms are methyl, ethyl, propyl, butyl, pentyl, hexyl, the n-isomers of all these residues, isopropyl, isobutyl, isopentyl, neopentyl, isohexyl, 3-methylpentyl, sec-butyl, tert-butyl, or tert-pentyl.

As used herein, the term "cycloalkyl" can be monocyclic or polycyclic, for example monocyclic, bicyclic or tricyclic, i.e., they can for example be monocycloalkyl residues, bicycloalkyl residues and tricycloalkyl residues, provided they have a suitable number of carbon atoms and the parent hydrocarbon systems are stable. A bicyclic or tricyclic cycloalkyl residue has to contain at least 4 carbon atoms. In an embodiment, a bicyclic or tricyclic cycloalkyl residue contains at least 5 carbon atoms. In a further embodiment, a bicyclic or tricyclic cycloalkyl residue contains at least 6 carbon atoms and up to the number of carbon atoms specified in the respective definition. Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_1$-$C_4$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

As used herein, the term "aryl" means an aromatic substituent which is a single ring or multiple rings fused together. When formed of multiple rings, at least one of the constituent rings is aromatic. In an embodiment, aryl substituents include phenyl, naphthyl and anthracyl groups.

The term "heteroaryl", as used herein, is understood as being unsaturated rings of five or six atoms containing one or two O- and/or S-atoms and/or one to four N-atoms, provided that the total number of hetero-atoms in the ring is 4 or less. The heteroaryl ring is attached by way of an available carbon or nitrogen atom. Non-limiting examples of heteroaryl groups include 2-, 3-, or 4-pyridyl, 4-imidazolyl, 4-thiazolyl, 2- and 3-thienyl, and 2- and 3-furyl. The term "heteroaryl", as used herein, is understood as also including bicyclic rings wherein the five or six membered ring containing O, S and N-atoms as defined above is fused to a benzene or pyridyl ring. Non-limiting examples of bicyclic rings include but are not limited to 2- and 3-indolyl as well as 4- and 5-quinolinyl.

It was surmised that if a fluorogen was prepared bearing two maleimide groups, then its latent fluorescence would only be realized upon its reaction with two equivalents of thiol. Furthermore, if the positioning of the maleimide groups was such that they were separated by a pre-determined distance, then the resulting fluorogen should react rapidly and specifically with compounds presenting two sulfhydryl groups separated by the corresponding distance.

Probe protein targets were designed to react efficiently with their complementary dimaleimide groups, through two cysteine residues whose pendant thiol groups would be solvent exposed, sterically unhindered and separated by an appropriate distance, namely that between the corresponding maleimide groups, as determined by molecular modeling. Small α-helical proteins (~about 30 amino acids) were selected as probe protein targets since their secondary structural motif is of sufficiently limited conformational flexibility so as to allow the precise positioning of the cysteine residues. Furthermore, the mass of these probe proteins is around one-tenth of the mass added in previous GFP-based assays, representing much less perturbation of native protein localization and function and allowing greater sensitivity for detection of biologically relevant events. With two cysteine residues positioned at a fixed geometry, spatially separated by a defined distance, these probe proteins will be able to react with the dimaleimide fluorogenic compounds, forming a fluorescent covalent adduct.

The novel fluorogenic markers and labeling method of the present disclosure comprises several features making it appropriate for genomic screening of molecular interactions: 1) the markers and method are not limited in their application to a single assay, but are capable of being used in a series of assays in which the fluorogen and protein target sequence may be chosen according to their efficacy in a particular cell type appropriate to the study of the interactions of a given class of proteins; 2) the method can be automated and tailored for high-throughput fluorescent screening; and 3) the markers are designed at the level of the atomic structure and three-dimensional conformation of the target protein motifs, allowing control over the flexibility and specificity of the probe fragments used.

The fluorogenic labeling method of the present disclosure has the potential to improve upon existing methods: 1) the relatively small probe proteins that are used in the method of the present disclosure have a far smaller potential to disrupt the localization and interactions of the native proteins than the relatively large protein fragments used in other methods; 2) the signal reaction being a simple reaction between a pair of protein-thiols and a thiol-selective small molecule fluorogen, it is less sensitive to the effects of variation of cellular conditions than the folding of fluorescent protein applications; and 3) the inherent flexibility of the method of the present disclosure to design fluorogenic probes with many different spectral qualities that react specifically with different protein targets provides for the encoding of protein interactions in a variety of ways, including the potential for multiplexed protein expression analysis in vivo and in vitro.

Maleimide groups are known for undergoing specific thiol addition reactions. They have been used in the context of analytical chemistry for the detection of thiols, based on the specificity of their reaction [19] and have been applied with success to protein labeling in vivo [4]. Their ability to quench fluorescence is also well-known [15]. It was surmised that a latent fluorophore bearing two maleimide groups would have to react at both maleimide groups in order to fluoresce, since one unreacted maleimide group would be sufficient to quench fluorescence.

In an embodiment, the present disclosure relates to fluorogens bearing two maleimide groups separated by distance that is defined by their conformational rigidity. In an embodiment, the dimaleimide fluorogens are designed to react with peptide sequences bearing two cysteine residues separated by a complementary distance (Scheme 1).

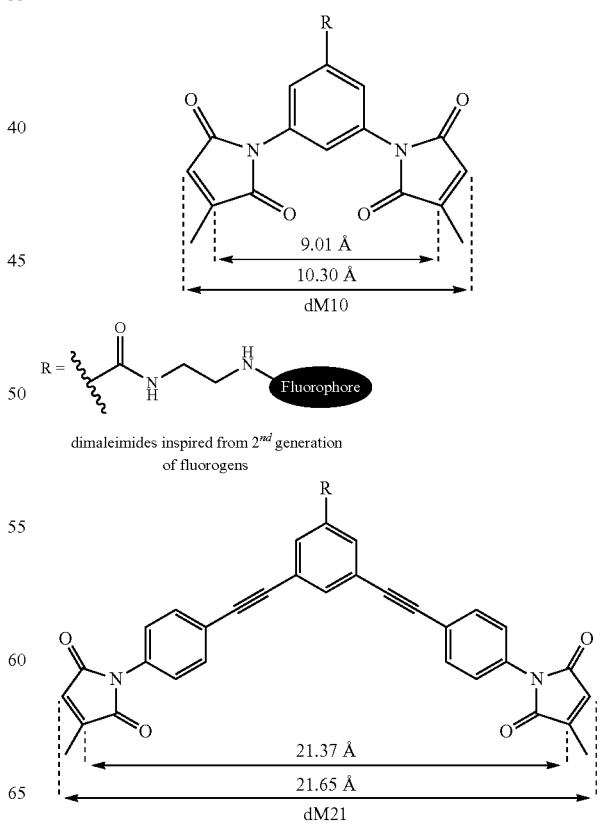

Scheme 1

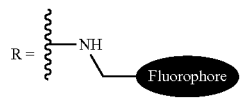

dimaleimides inspired from
3$^{rd}$ generation
of fluorogens

SYNTHESIS OF FLUOROPHORES

In order to minimize the distance between the dimaleimide fragment and its fluorophore, and hence improve on the fluorescence quench efficiency, fluorogens were designed comprising a structure in which the fluorophore is directly attached to a modified dimaleimide fragment.

Synthesis of Fluorogen 5

The synthesis of the dimaleimide fragment was initiated starting with 3,5-dinitrobenzoic acid undergoing a Schmidt rearrangement, leading quantitatively to the 3,5-dinitroaniline (1). The 3,5-dinitroaniline (1) was then submitted to catalytic hydrogenation and a mono Boc protection, giving triamine (2) as a base scaffold for the dimaleimide fragment. The mono-protected phenylenetriamine was then reacted with excess citraconic anhydride, leading to the dimaleamic acid derivative which was then cyclized to the dimaleimide core (3) upon treatment with HMDS and ZnCl$_2$. The fluorogen (5) was obtained by deprotection of the Boc group with excess TFA and coupling of the corresponding aniline with dansyl chloride in pyridine (Scheme 2).

Scheme 2

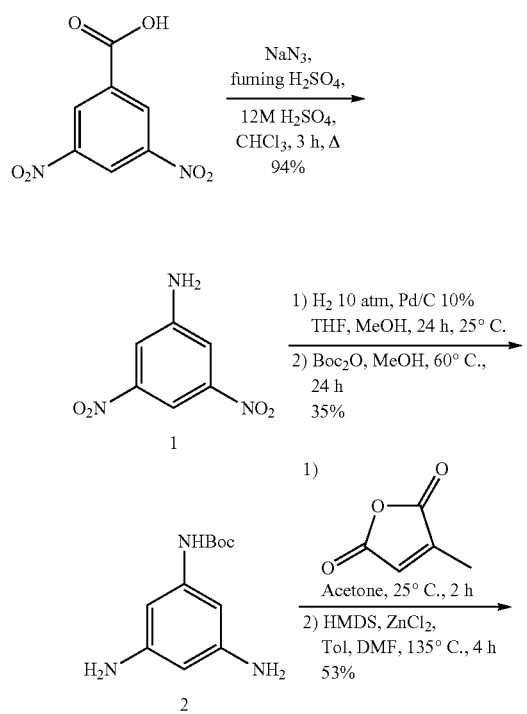

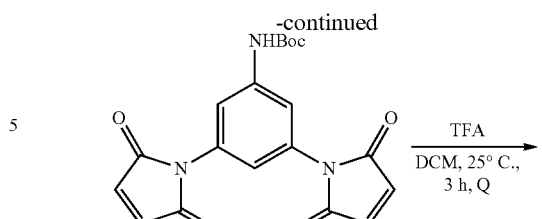

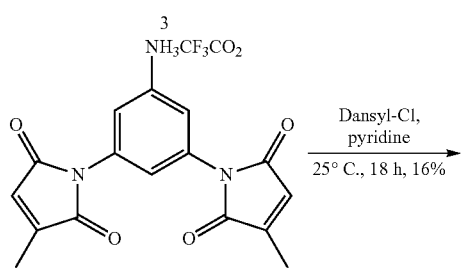

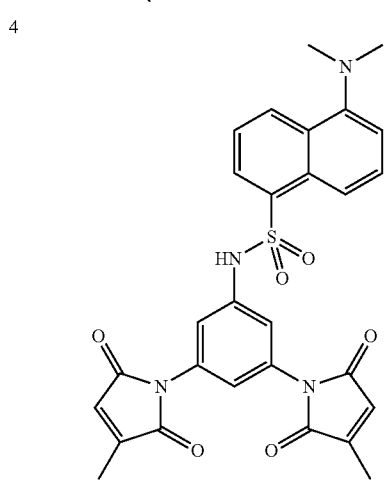

Spectroscopic characterization of fluorogen 5 included absorbance and fluorescence emission maxima as well as the fluorescence enhancement (FE) ratio. The spectroscopic characteristics were evaluated in two solvent systems (DMSO and HEPES (pH 7.4)/5% DMSO). The FE ratio determination was carried out by reacting 5 with excess mercaptopropionic acid (MPA) and then dividing the final fluorescence by the initial fluorescence intensity, at a specific fluorogen concentration. In pure DMSO, the initial fluorescence intensity was found to be approximately 2, where upon reaction with MPA the fluorescence intensity increased by over 300-fold (FIG. 1). In aqueous media (HEPES/5% DMSO) the initial fluorescence intensity was at the level of the background noise, leading to a fluorescence enhancement ratio of over 175.

Synthesis of Fluorogen 11

The synthesis of the dimaleimide fragment was initiated starting with 3,5-dinitrobenzoic acid undergoing reduction with sodium borohydride to provide 3,5-dinitrobenzylic alcohol 6. Protected amine 7 was obtained by using phthalimide as a nucleophile under Mitsonobu conditions. Subsequent exchange of protecting groups provided Boc-protected amine 8. Treatment of 8 with TFA and coupling of the resulting free amine with 7-methoxycoumarin-3-carboxylic acid resulted in compound 9 which was subsequently submitted to catalytic hydrogenation providing diamine 10. The fluorogen (11) was obtained by reaction of 10 with citraconic anhydride and subsequent cyclization of the in situ generated dimaleamic acid (Scheme 3).

Scheme 3

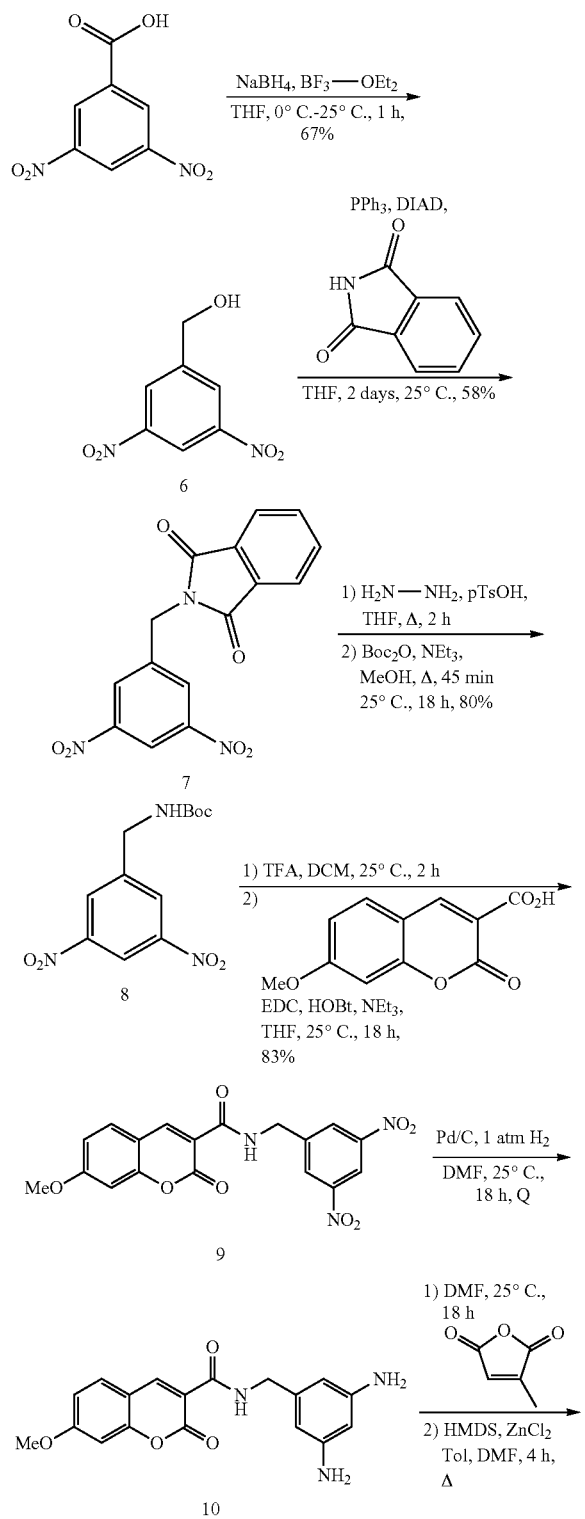

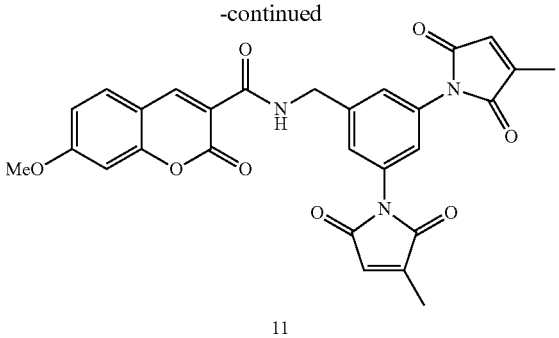

11

Figure 2:
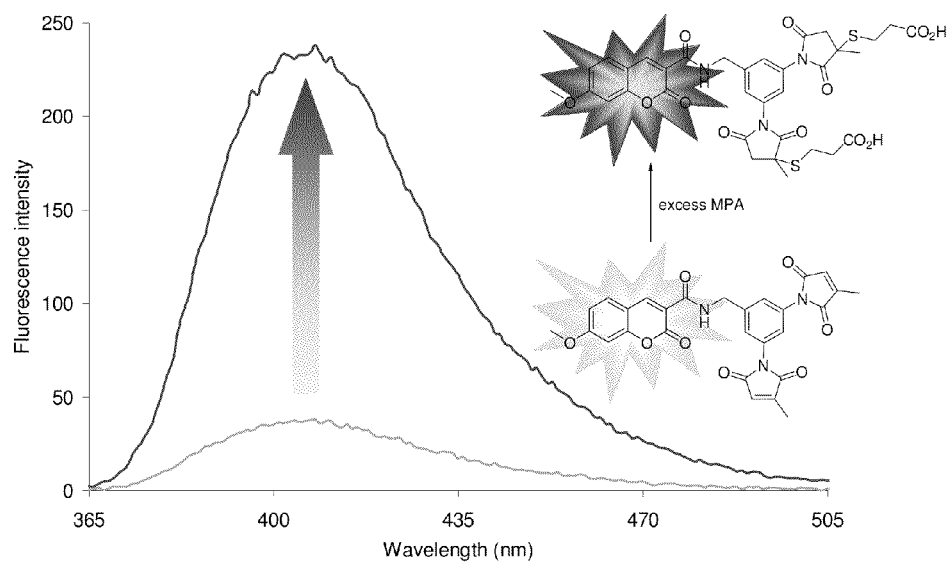
FIG. 2 is an illustration of the fluorescence enhancement ratio (FE) of fluorogen 11 when reacted with excess MPA ($\lambda_{ex}$=347 nm, HEPES/DMSO 5%)

Spectroscopic characterization of fluorogen 11 included absorbance and fluorescence emission maxima as well as the fluorescence enhancement (FE) ratio. The spectroscopic characteristics of 11 were evaluated in HEPES (pH 7.4)/5% DMSO). The FE ratio determination was carried out by reacting 11 with excess mercaptopropionic acid (MPA) and then dividing the final fluorescence by the initial fluorescence intensity, at a specific fluorogen concentration. Upon reaction with excess MPA the fluorescence intensity increased by a factor of 6.4 (FIG. 2).

Synthesis of Fluorogen 13

The synthesis of the dimaleimide fragment 12 was initiated starting with 3,5-diaminobenzoic acid undergoing reaction with citraconic anhydride and subsequent cyclization of the in situ generated dimaleamic acid. The BODIPY fluorogen 13 was obtained following the condensation reaction of two pyrroles with the acyl chloride of 12 and subsequent oxidation and complexation with trifluoroboron diethyl etherate (Scheme 4). The BODIPY fluorophore of 13 is attached to the dimaleimide core by a simple sigma bond, conferring great conformational rigidity between the two fragments.

Scheme 4

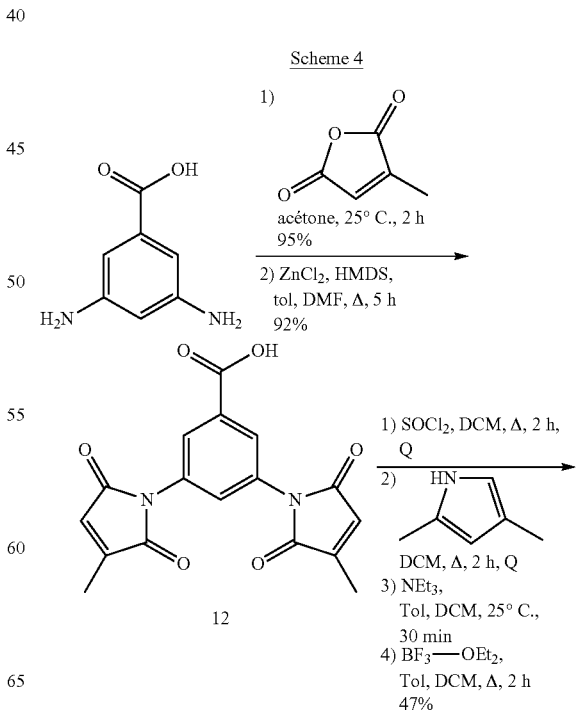

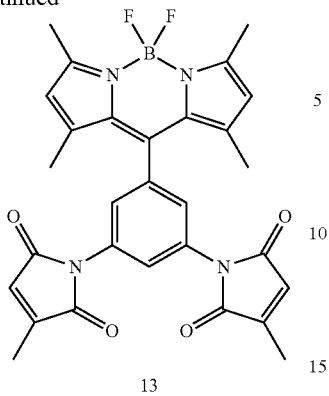

13

Figure 3:
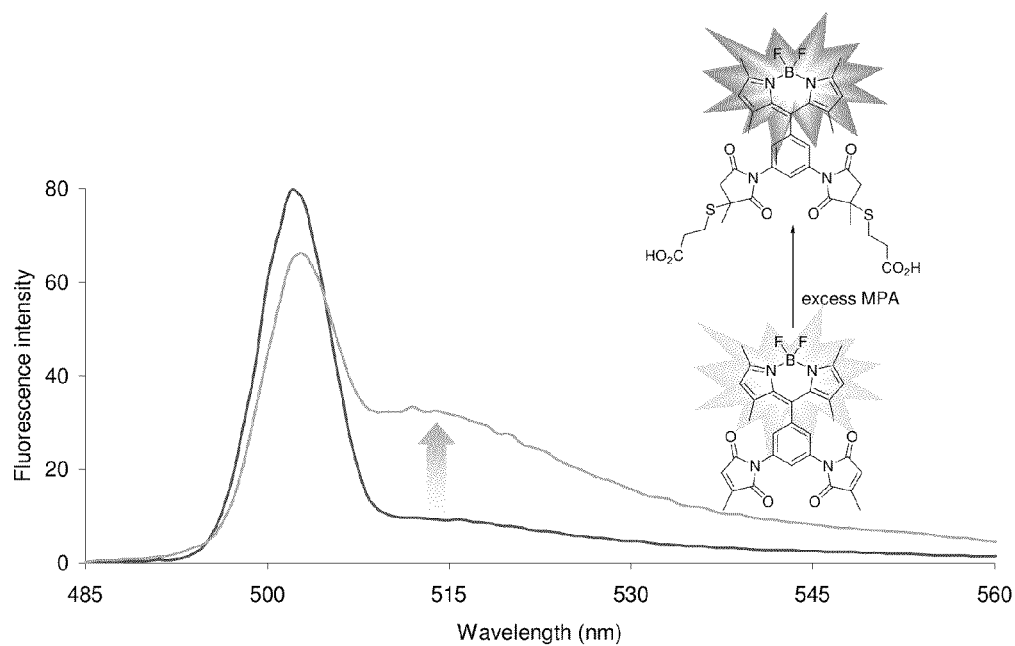
FIG. 3 is an illustration of the fluorescence enhancement ratio (FE) of fluorogen 13 when reacted with excess MPA ($\lambda_{ex}$=502 nm, HEPES/DMSO 5%)
Figure 4:
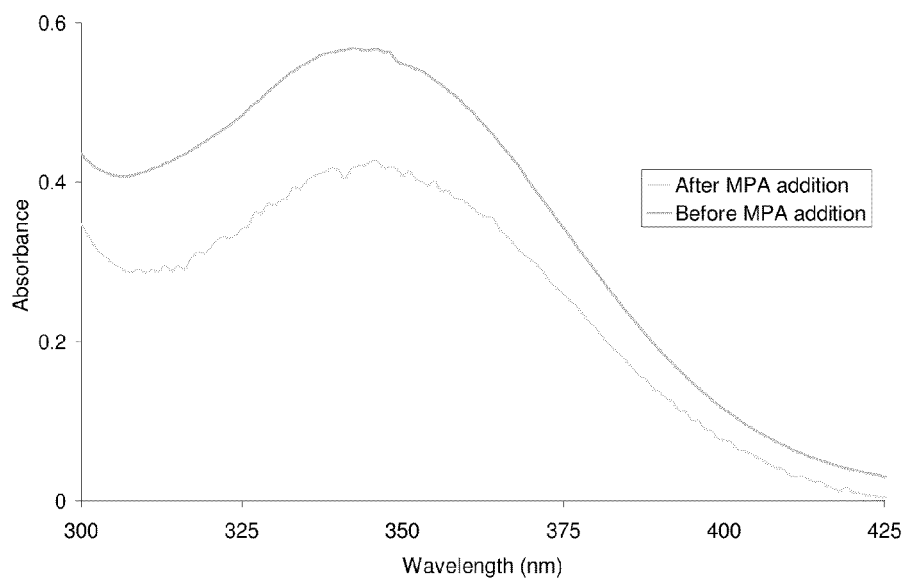
FIG. 4 is an illustration of the absorbance maxima of fluorogen 5 (DMSO, 500 µM)
Figure 5:
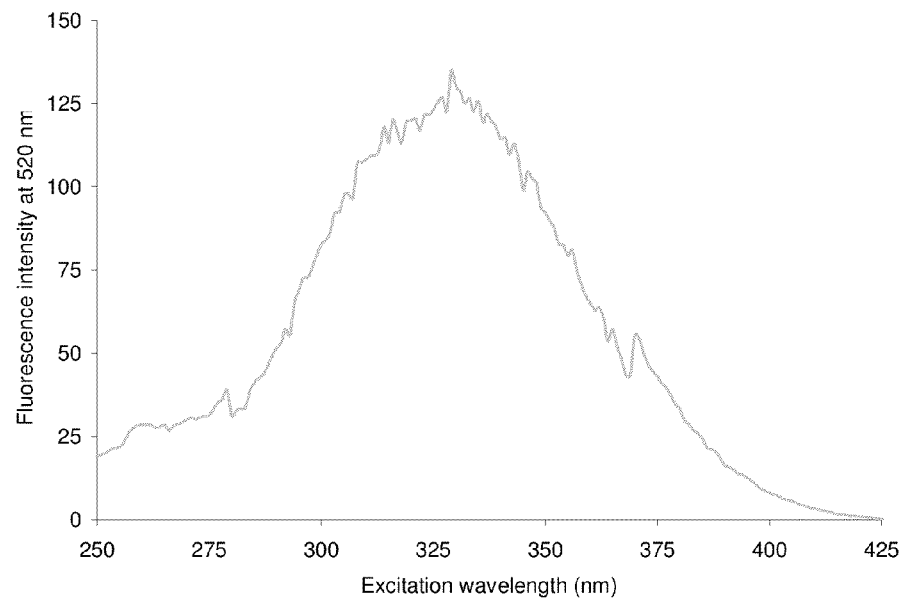
FIG. 5 is an illustration of the excitation maxima of the fluorogen 5-diMPA adduct (HEPES/DMSO 5%, 200 µM)
Figure 6:
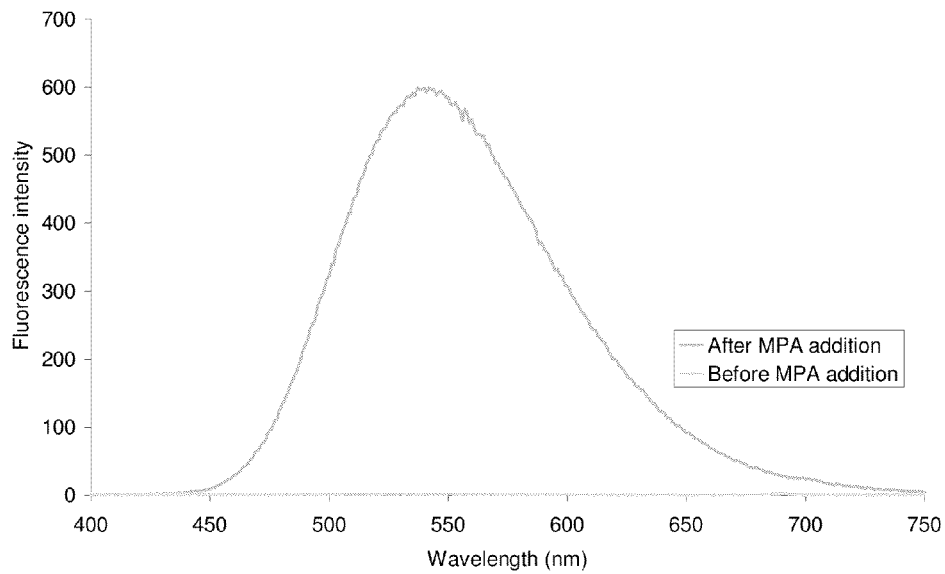
FIG. 6 is an illustration of the fluorescence emission maxima of fluorogen 5 and its di-MPA adduct (DMSO, 250 µM)
Figure 7:
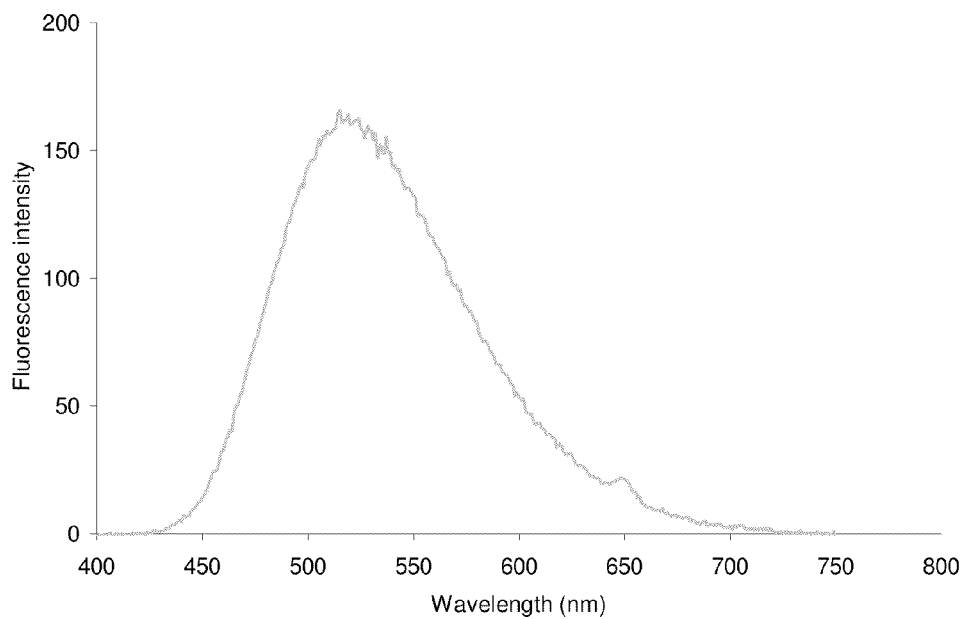
FIG. 7 is an illustration of the fluorescence emission maxima of fluorogen 5 (HEPES/DMSO 5%, 100 µM)
Figure 8:
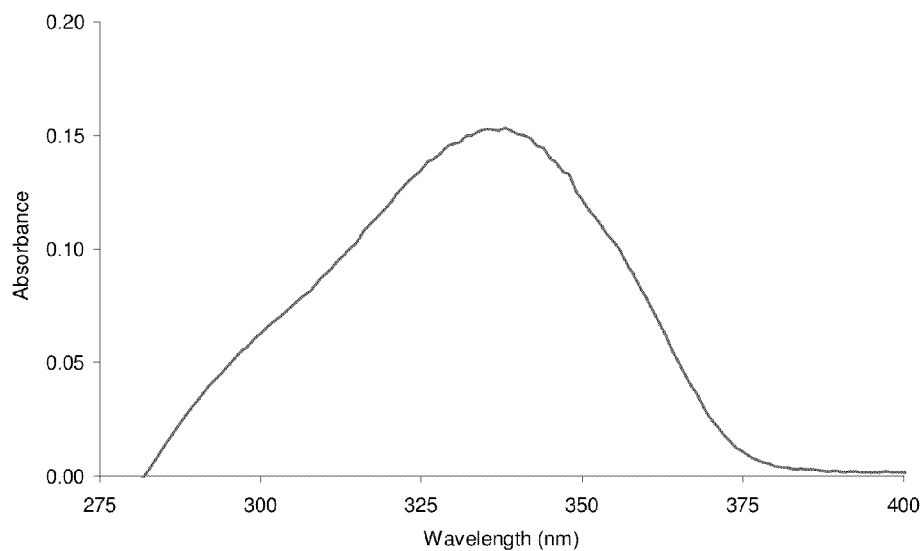
FIG. 8 is an illustration of the absorbance maxima of fluorogen 11 (HEPES/DMSO 5%, 50 µM)
Figure 9:
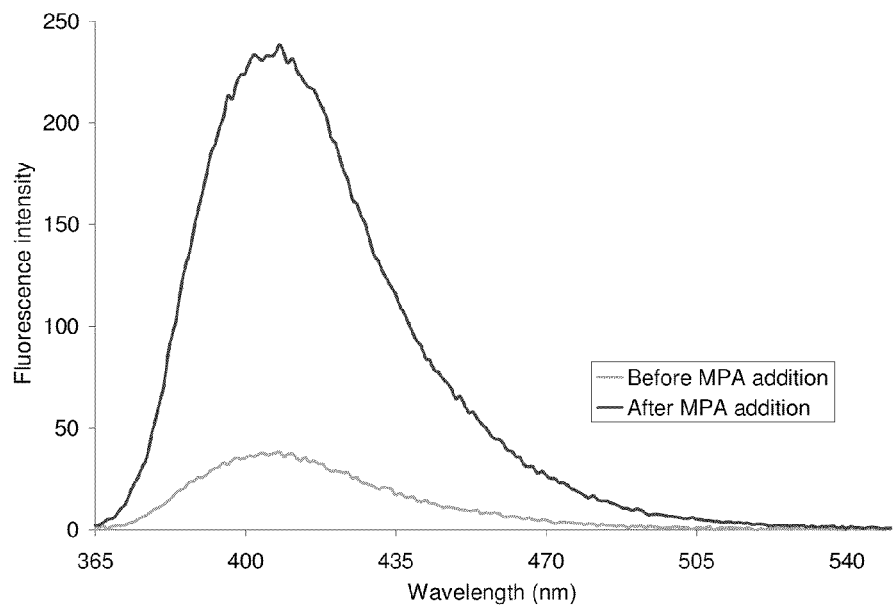
FIG. 9 is an illustration of the fluorescence emission maxima of fluorogen 11 and its di-MPA adduct (HEPES/DMSO 5%, 4 µM)
Figure 10:
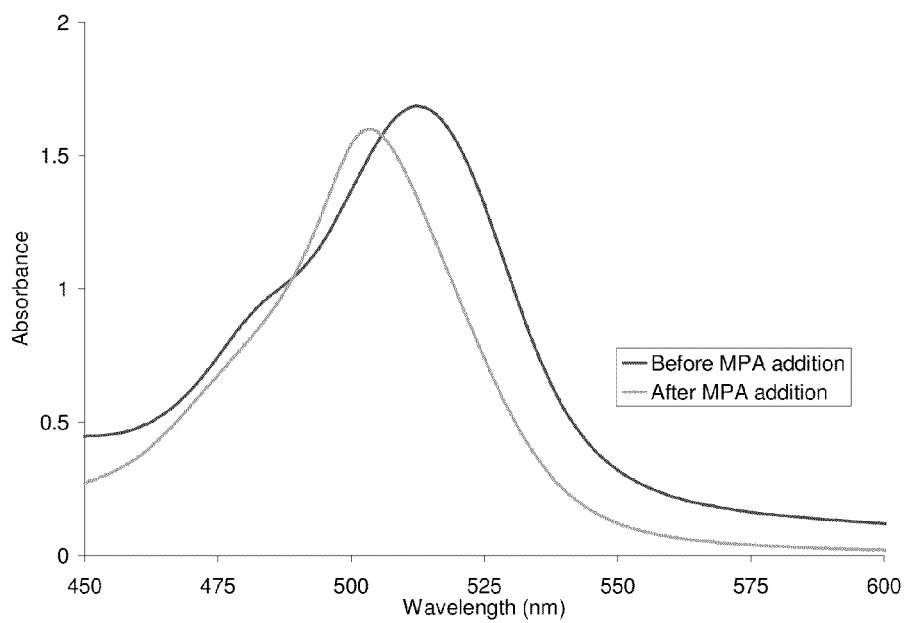
FIG. 10 is an illustration of the absorbance maxima of fluorogen 13 and its di-MPA adduct (HEPES/DMSO 5%, 20 µM)
Figure 11:
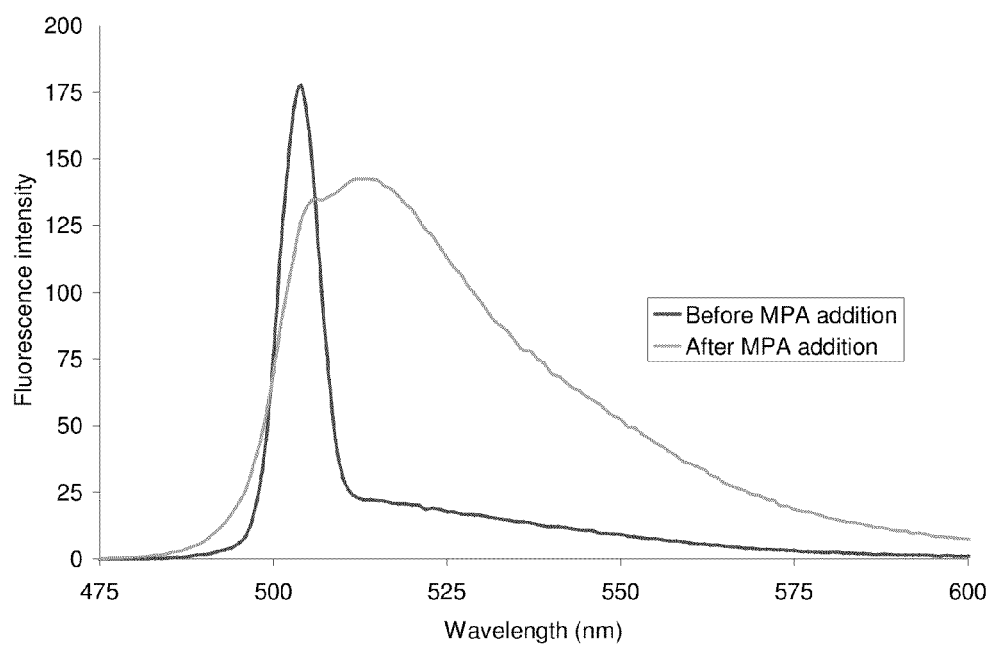
FIG. 11 is an illustration of the fluorescence emission maxima of fluorogen 13 and its di-MPA adduct (HEPES/DMSO 5%, 1 µM)

Spectroscopic characterization of fluorogen 13 included absorbance and fluorescence emission maxima as well as the fluorescence enhancement (FE) ratio. The spectroscopic characteristics of 13 were evaluated in HEPES (pH 7.4)/5% DMSO). The FE ratio determination was carried out by reacting 13 with excess mercaptopropionic acid (MPA) and then dividing the final fluorescence by the initial fluorescence intensity, at a specific fluorogen concentration. Upon reaction with excess MPA the fluorescence intensity increased by a factor of 3.5 (FIG. 3).

Synthesis of Fluorogen 17

Fluorogen 17 was designed to bring the maleimide groups closer to the fluorescent moiety. The synthesis of fluorogen 21 is presented in Scheme 5. Diiodination of benzoic acid, followed by a double Sonogashira coupling with Boc protected p-ethynylaniline according to standard coupling conditions afforded intermediate 15. Removal of the Boc groups with TFA, followed by reaction with citraconic anhydride and further cyclization by treatment with Ac$_2$O and NaOAc provided intermediate 16. Treatment of 16 with 2,4-dimethylpyrrole and BF$_3$—OEt$_2$ completed the synthesis fluorogen 17.

Scheme 5

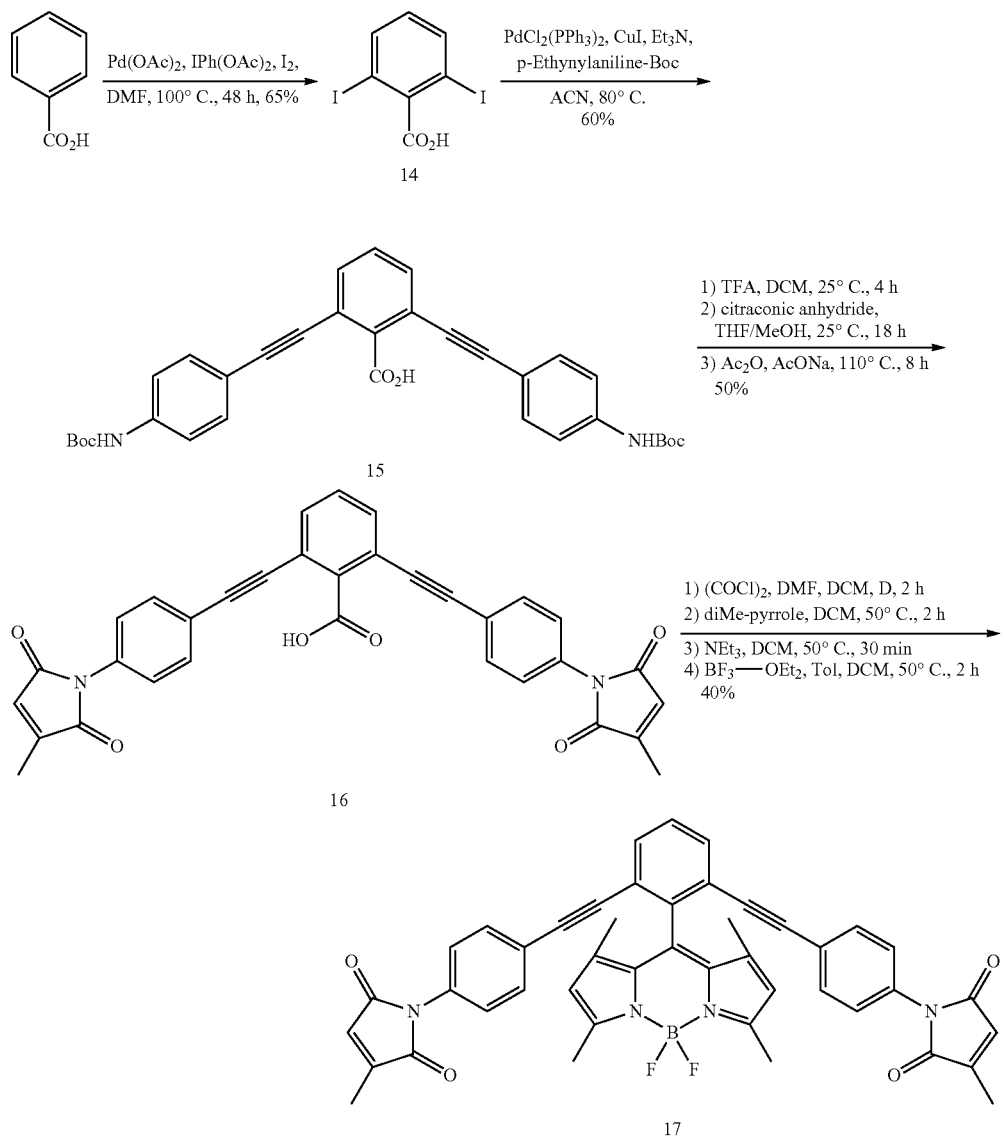

Figure 12:
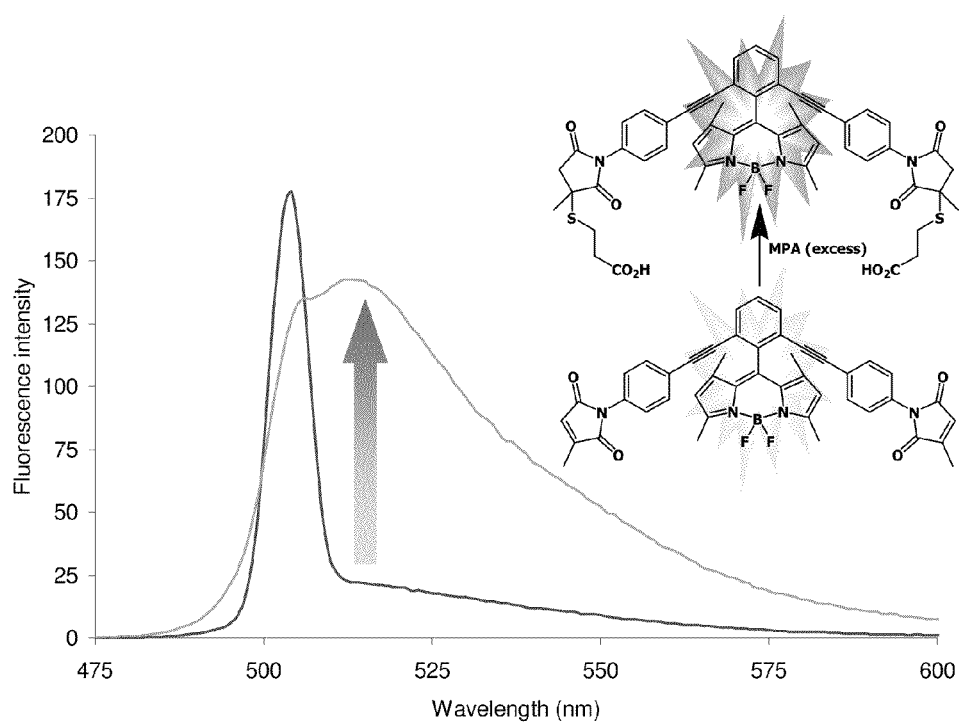
FIG. 12 is an illustration of the fluorescence enhancement ratio (FE) of fluorogen 17 when reacted with excess MPA ($\lambda_{ex}$=502 nm, HEPES/DMSO 5%)

Spectroscopic characterization of fluorogen 17 included absorbance and fluorescence emission maxima as well as the fluorescence enhancement (FE) ratio. The spectroscopic characteristics of 17 were evaluated in HEPES (pH 7.4)/5% DMSO). The FE ratio determination was carried out by reacting 17 with excess mercaptopropionic acid (MPA) and then dividing the final fluorescence by the initial fluorescence intensity, at a specific fluorogen concentration. Upon reaction with excess MPA the fluorescence intensity increased by a factor of 6.4 (FIG. 12).

Synthesis of Fluorogen 21

Fluorogen 21 comprises a fluorophore which is connected to the dimaleimide fragment through a benzylic amine linkage. This type of linkage allows for additional conformational flexibility whereby the maleimide group can approach the fluorophore more closely, allowing for more significant quenching. Reduction of aldehyde with NaBH$_4$ provided the corresponding alcohol 18 which was subjected to a Mitsunobu reaction to yield the corresponding phthalimide derivative 19. Treatment of the benzylic phthalimide with hydrazine provided the free amine which was subsequently coupled to the fluorophore [e.g. dansyl-Cl, FITC and coumarin-CO$_2$H]. Double Sonogashira coupling of 20 with p-alkyne-maleimido-phenyl completed the synthesis fluorogen 21. (Scheme 6).

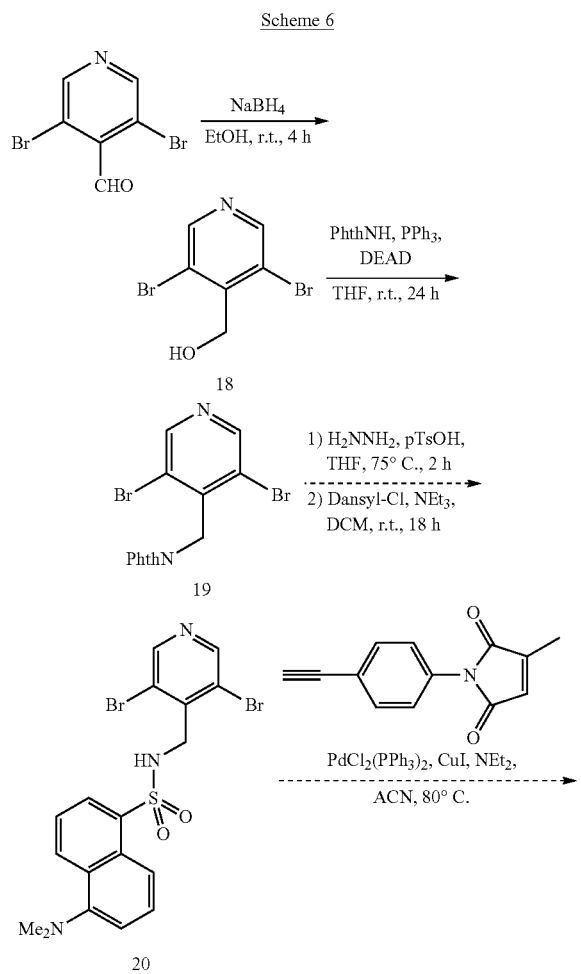

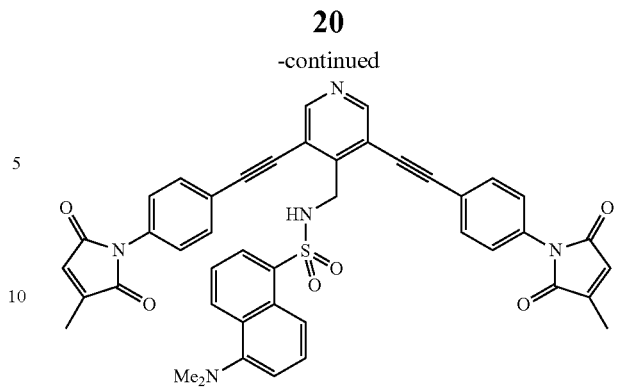

Selected photophysical properties of fluorogens 5, 11 and 13 and corresponding di-MPA adducts obtained by reaction with excess MPA, are illustrated in Table 1.

TABLE 1

Photophysical properties fluorogens 5, 11 and 13 and corresponding di-MPA adducts obtained by reaction with excess MPA.

| Fluorogen | $\lambda_{ex}/\lambda_{em}$ (nm) DMSO | $\lambda_{ex}/\lambda_{em}$ (nm) HEPES/ DMSO 5% | $\lambda_{ex}/\lambda_{em}$ (nm) MPA adduct DMSO | $\lambda_{ex}/\lambda_{em}$ (nm) MPA adduct HEPES/ DMSO 5% | FE HEPES/ DMSO 5% |
|---|---|---|---|---|---|
| 5 | 345/540 | 325/520 | 350/540 | 325/520 | >175 |
| 11 |  | 347/404 |  | 347/404 | 6.4 |
| 13 |  | 510/514 |  | 510/514 | 3.5 |

EXPERIMENTAL

All starting materials were obtained commercially from Sigma-Aldrich and used without further purification. Solvents were dried using GlassContour System (Irvine, Calif.) columns. Reactions requiring anhydrous conditions were carried out under a dry nitrogen atmosphere employing conventional benchtop techniques. $^{13}$C and $^1$H NMR spectra were recorded on AMXR400 and AMX300 spectrometers and were referenced to the residual proton or $^{13}$C signal of the solvent. Mass spectra were determined by FAB+ ionization on an AutoSpec Q spectrometer at the Regional Mass Spectrometry Centre at the Université de Montréal. Melting points (uncorrected) were determined on an EZ-Melt (SRS) melting point apparatus.

Determination of Fluorescence Enhancement Ratios

Absorbance spectra were recorded at 25° C., with a Cary-100 spectrometer. Emission spectra and fluorescence intensity measurements were recorded at 25° C. with a Cary Eclipse fluorometer. Excitation and emission slits were fixed at 5 nm.

Protocol: 3-Mercaptopropionic acid (50 eq) was added to a 1 to 4 mM DMSO solution of fluorogen. The resulting mixture was stirred at 25° C., in the dark for 18 hours after which fluorescence intensities of a dilution in HEPES buffer (pH 7.4) were recorded. Final fluorescence intensity was then divided by the initial florescence intensity at the same fluorogen concentration leading to the fluorescence enhancement ratio for the fluorogen.

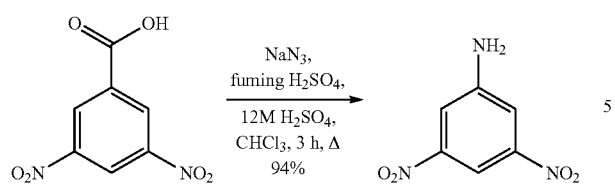

3,5-Dinitroaniline (1): To a solution of 3,5-dinitrobenzoic acid (4.0 g, 18.9 mmol) in a mixture of concentrated sulfuric acid (6 mL), 30% fuming sulfuric acid (18 mL) and $CHCl_3$ (25 mL) was added sodium azide (1.4 g, 21.7 mmol), in small portions. The resulting mixture was heated to reflux (80° C.) for 3 hours and then cooled to 25° C. after which it was poured on ice. An orange solid was isolated after vacuum filtration (3.25 g, 17.7 mmol, 94%). $^1$H NMR (300 MHz, $CDCl_3$) δ 8.14 (t, J=1.8 Hz, 1H), 7.64 (d, J=1.8 Hz, 2H), 4.39 (s (br), 2H); $^{13}$C NMR (75 MHz, $CDCl_3$) δ 151.9, 150.1, 113.1, 105.2; HRMS (ESI) Calculated for $C_6H_4N_3O_4$ [M−H]$^-$: 182.0195. Found: 182.0207. m.p.: 113.1° C.

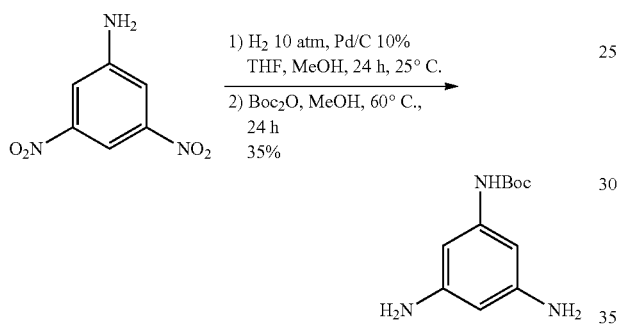

tert-Butyl N-3,5-diaminophenylcarbamate (2): A solution of 1 (2.3 g, 12.56 mmol) in THF/MeOH (30/5 mL) in the presence of Pd/C 10% (50% w/w $H_2O$) was stirred at room temperature under hydrogen (10 atm.) for 24 h after which the solvents were filtered on celite. The resulting phenylenetriamine was used in the next step without further purification. The filtrate volume was increased to 200 mL after which a solution of $Boc_2O$ (2.7 g, 12.56 mmol) in THF (20 mL) was added over 30 minutes. The resulting solution was heated to reflux for 16 hours after which volatiles were evaporated under reduced pressure. The crude was then purified by flash chromatography on silica gel (elution gradient DCM/Hex (8:2) to DCM/MeOH (49:1)) to give 2 (958 mg, 4.29 mmol, 35%) as an off-white solid. $^1$H NMR (400 MHz, $CDCl_3$) δ 6.18 (d, J=2 Hz, 2H), 5.95 (bs, 1H), 5.73 (t, J=2.0 Hz, 1H), 3.57 (bs, 4H), 1.50 (bs, 9H); $^{13}$C NMR (100 MHz, $CDCl_3$) δ 152.5, 148.0, 140.1, 96.8, 96.0, 80.1, 28.2; HRMS (ESI) Calculated for $C_{11}H_{17}N_3O_2Na$ [M+Na]$^+$: 246.1218. Found: 246.1214.

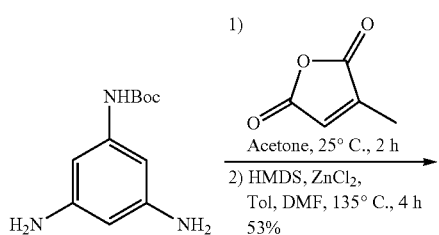

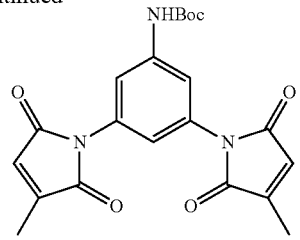

tert-Butyl N-3,5-di-(2-methylmaleimido)phenylcarbamate (3): Citraconic anhydride (1.56 mL, 17.47 mmol) was added to a solution of 2 (1.3 g, 5.82 mmol) in $CHCl_3$ (20 mL) and the resulting mixture was stirred at 25° C. for 3 hours after which volatiles were evaporated under reduced pressure. The crude was triturated with $Et_2O$ and filtered under reduced pressure giving the dimaleamic acid as a beige solid (2.59 g, 5.80 mmol, quantitative) that was used in the next step without further purification.

Dimaleamic acid (400 mg, 0.894 mmol) and $ZnCl_2$ (365 mg, 2.68 mmol) were dissolved in toluene/DMF (40:5 mL) after which a dilute solution of HMDS (0.84 mL, 4.02 mmol) in toluene (5 mL) was added over 20 minutes. The resulting mixture was then heated to reflux for 4 hours after which the volatiles were evaporated under reduced pressure. The resulting residue was dissolved in EtOAc and washed successively with 0.1 M HCl and saturated $Na_2CO_3$. The crude product was then purified by flash chromatography on silica gel (Toluene/EtOAc 5%) to give 3 as an off-white solid (780 mg, 1.90 mmol, 53%). $^1$H NMR (400 MHz, $CDCl_3$) δ 7.42 (d, J=2.4 Hz, 2H), 7.12 (t, J=2.4 Hz), 6.59 (bs, 1H), 6.43 (q, J=2.4 Hz, 2H), 2.12 (q, J=2.4 Hz, 6H), 1.47 (bs, 9H); $^{13}$C NMR (75 MHz, $CDCl_3$) δ 170.0, 168.9, 152.2, 145.7, 139.5, 132.5, 127.4, 116.5, 114.1, 80.9, 28.1, 11.0; HRMS (ESI) Calculated for $C_{21}H_{21}N_3O_6Na$ [M+Na]$^+$: 434.1331. Found: 434.1323. m.p.: 179° C.

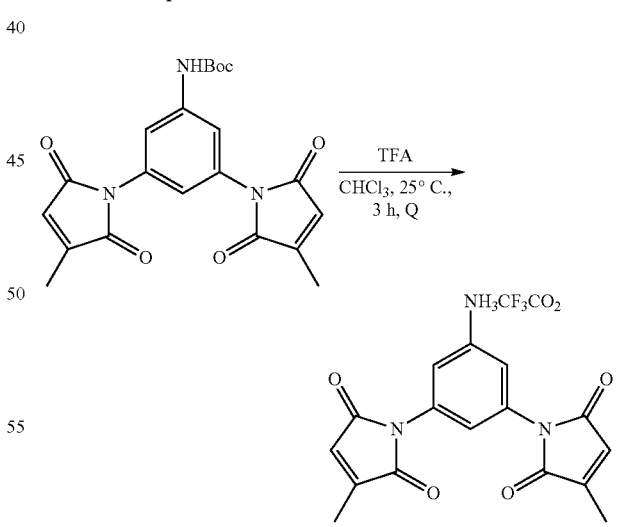

3,5-Di-(3-methylmaleimido)anilinium trifluoroacetate (4): A solution of 3 (780 mg, 1.90 mmol) in $CHCl_3$ (10 mL) was treated with TFA (5.9 mL, 76 mmol) at 25° C. for 3 hours after which the volatiles were evaporated. An off-white solid was then precipitated with $Et_2O$ (805 mg, 1.89 mmol, Quantitative). The TFA salt 4 was used in the next step without further purification.

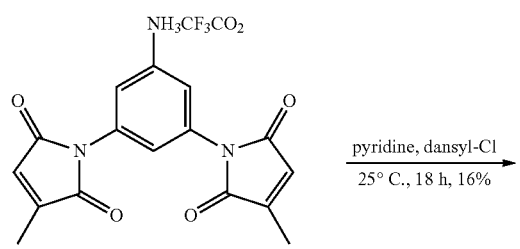

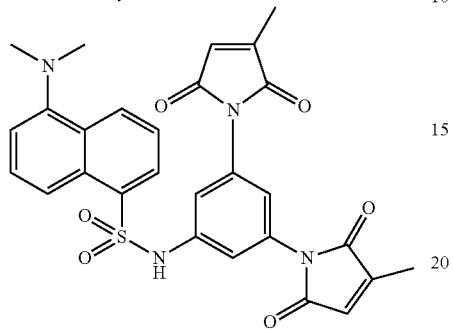

N-Dansyl-3,5-di-(3-methylmaleimido)aniline (5): Dansyl chloride (139 mg, 0.517 mmol) in pyridine (3 mL) was added to a pyridine solution of 4 (200 mg, 0.517 mmol). The resulting mixture was stirred at 25° C. for 18 hours after which the volatiles were evaporated under reduced pressure. The resulting oil was taken back in CHCl$_3$ and the organic phase was washed with aqueous saturated Na$_2$CO$_3$, dried over MgSO$_4$ and evaporated. The crude was purified by flash chromatography on silica gel (Tol/EtOAc 10%) giving 5 as a light green solid (40 mg, 0.074 mmol, 16%). $^1$H NMR (400 MHz, (CD$_3$)$_2$CO) δ 9.71 (s, 1H), 8.56 (d, J=8.4 Hz, 1H), 8.51 (d, J=8.8 Hz, 1H), 8.39 (dd, J$_1$=1.2, 7.2 Hz, 1H), 7.62-7.58 (td, J=1.2, 7.2 Hz, 2H), 7.28-7.27 (m, 3H), 7.11 (t, J=2.0 Hz, 1H), 6.63-6.61 (m, 2H); $^{13}$C NMR (75 MHz, (CD$_3$)$_2$CO) δ 171.3, 170.4, 152.8, 135.4, 134.0, 131.7, 131.5, 130.3, 130.2, 129.6, 128.7, 124.9, 119.8, 119.6, 116.6, 115.9, 46.3, 12.1; HRMS (ESI) Calculated for C$_{28}$H$_{25}$N$_4$O$_6$S [M+H]$^+$: 545.1516. Found: 545.1489. m.p.: 230° C.

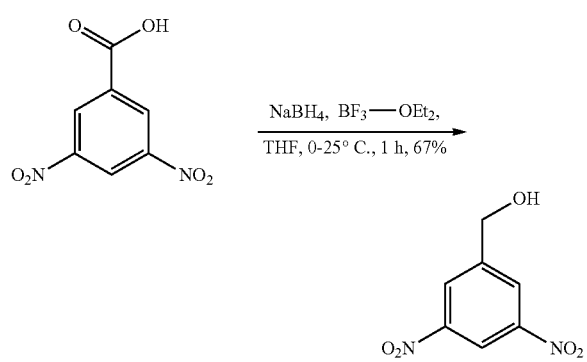

(3,5-Dinitrophenyl)methanol (6): To a suspension of NaBH$_4$ (2.85 g, 75.4 mmol) in dry THF (40 mL) at 0° C. was added a solution of 3,5-dinitrobenzoic acid (8.0 g, 37.7 mmol) in THF (20 mL), followed by the addition of BF$_3$.OEt$_2$ (12.5 mL, 98.0 mmol). The resulting mixture was warmed to 25° C. and stirred for 1 hour after which the reaction was quenched with 1 M HCl. The aqueous phase was extracted with DCM and the organic phase was then washed with saturated Na$_2$CO$_3$. The organic phase was dried over MgSO$_4$ and evaporated under reduced pressure to give the title compound 6 as an orange solid (5.01 g, 25.3 mmol, 67%). $^1$H NMR (400 MHz, ((CD$_3$)$_2$C)) δ 8.91 (t, J=0.4 Hz, 1H), 8.57 (dd, J=1.2, 2.0 Hz, 2H), 4.93 (d, J=5.2 Hz, 2H), 3.57 (bs, 1H); $^{13}$C NMR (75 MHz, (CD$_3$)$_2$CO) δ 149.4, 148.4 (2C), 127.0 (2C), 117.6, 62.8; HRMS (ESI) Calculated for C$_7$H$_5$N$_2$O$_5$ [M−H]$^-$: 197.0204. Found: 197.0200. m.p.: 89° C.

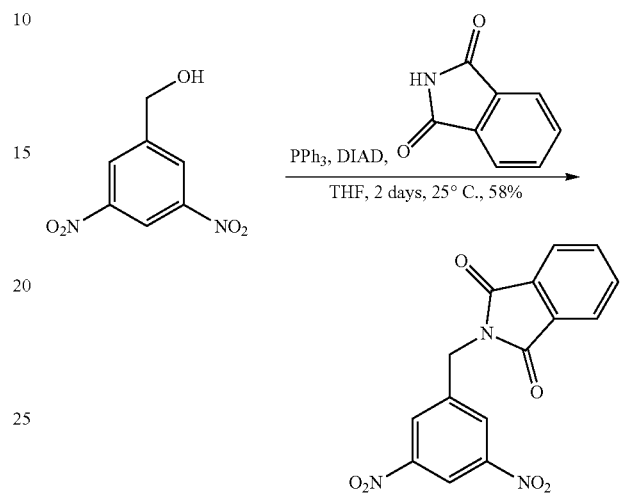

N-(3,5-dinitrophenyl)methylphthalimide (7): To a solution of 3,5-dinitrobenzylic alcohol 6 (1.38 g, 6.94 mmol), triphenylphosphine (2.19 g, 8.33 mmol) and phthalimide (1.23 g, 8.33 mmol) in dry THF (40 mL) was added DIAD (1.64 mL, 8.33 mmol) under an N$_2$ atmosphere. The resulting mixture was stirred at 25° C. for 48 hours after which solvents were evaporated under reduced pressure. The crude product mixture was triturated in EtOAc and filtered under reduced pressure to give the title compound 7 as a beige solid (1.33 g, 4.05 mmol, 58%). $^1$H NMR (400 MHz, CDCl$_3$) δ 8.98 (t, J=2.0 Hz, 1H), 8.61 (d, J=2.0 Hz, 2H), 7.93-7.89 (m, 2H), 7.81-7.77 (m, 2H), 5.05 (s, 2H); $^{13}$C NMR (75 MHz, CDCl$_3$) δ 168.5, 168.4, 149.6, 141.3, 135.5, 132.5, 129.6, 124.7, 119.3, 41.2; HRMS (ESI) Calculated for C$_{15}$H$_{10}$N$_3$O$_6$ [M+H]$^+$: 328.0564. Found: 328.0568. m.p.: 171° C.

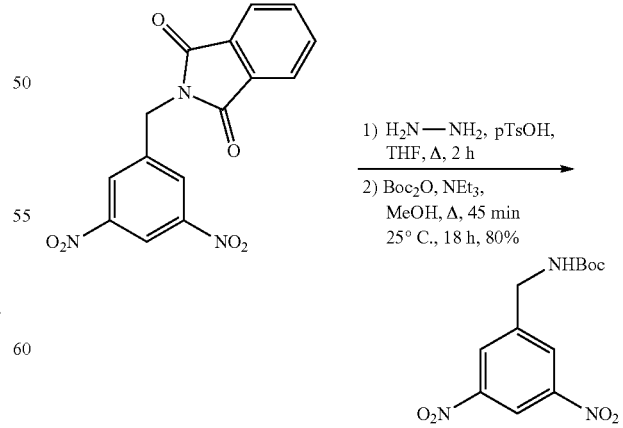

tert-Butyl N-3,5-dinitrobenzylcarbamate (8): To a solution of 7 (960 mg, 2.93 mmol) in THF (20 mL) were added hydrazine (1.14 mL, 23.4 mmol) and p-nitrotoluenesulfonic acid (280 mg, 1.47 mmol). The resulting mixture was heated to reflux for 2 hours after which it was cooled to 25° C. and saturated Na₂CO₃ was added. The aqueous phase was extracted with CHCl₃ and the organic fractions were combined, dried over MgSO₄ and evaporated under reduced pressure to give the free benzylic amine as a yellow solid that was used in the next step without further purification.

A solution of the benzylic amine in MeOH (20 mL) was treated with Boc₂O (1.28 g, 5.86 mmol) and NEt₃ (0.62 mL, 4.40 mmol). The resulting mixture was heated to reflux for 45 minutes and then stirred at 25° C. for 18 hours, after which solvents were evaporated. The crude product mixture was dissolved in CHCl₃ and the organic phase was washed with 0.1 M HCl, dried over MgSO₄ and evaporated under reduced pressure. The solid was purified by flash chromatography on silica gel (DCM/Hex 20%) to give the title compound 8 as a white solid (945 mg, 2.34 mmol, 80%). ¹H NMR (400 MHz, CDCl₃) δ 8.93 (bs, 1H), 8.49 (d, J=2.4 Hz, 2H), 5.28 (bs, 1NH), 4.52 (d, J=6.0 Hz, 2H), 1.47 (bs, 9H); ¹³C NMR (75 MHz, CDCl₃) δ 155.8, 148.4, 144.2, 127.1, 117.5, 80.6, 43.4, 28.1; HRMS (ESI) Calculated for $C_{12}H_{15}N_3O_6$ [M]⁻: 297.0963. Found: 297.0966. m.p.: 94° C.

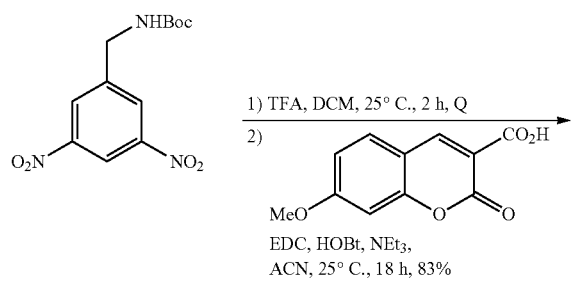

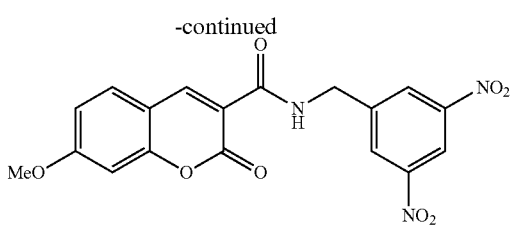

7-Methoxy-3-(3,5-dinitrobenzyl)aminocarbonylcoumarin (9): TFA (2.77 mL, 36 mmol) was added to a solution of the benzylic amine 8 ((267 mg, 0.898 mmol) in DCM (10 mL). The resulting mixture was stirred at 25° C. for 2 hours after which solvents were evaporated. Addition of Et₂O to the resulting oil led to the formation of a precipitate that was used in the next step without further purification.

A solution of the TFA salt in ACN (10 mL) was added to a solution of 7-methoxycoumarin-3-carboxylic acid (218 mg, 0.988 mmol), EDC (189 mg, 0.988 mmol), HOBt (134 mg, 0.988 mmol) and NEt₃ (0.26 mL, 1.89 mmol) in ACN (20 mL). The resulting mixture was stirred at 25° C. for 18 hours after which solvents were evaporated under reduced pressure. The crude reaction product mixture was dissolved in CHCl₃ and the organic phase was washed successively with saturated Na₂CO₃ and 0.1 M HCl, dried over MgSO₄ and evaporated under reduced pressure to give 9 as a beige solid (298 mg, 0.747 mmol, 83%). ¹H NMR (400 MHz, DMSO-d₆) δ 9.41 (t, J=5.6 Hz, 1H), 8.45 (s, 1H), 8.72 (t, J=2.0 Hz, 1H), 8.65 (d, J=2.0 Hz, 2H) 7.90 (d, J=8.8 Hz, 1H), 7.13 (d, J=2.4 Hz, 1H), 7.05 (dd, J=2.4, 8.8 Hz, 1H), 4.75 (d, J=6.0 Hz, 1H), 3.92 (s, 3H); ¹³C NMR (75 MHz, DMSO-d₆) δ 165.0, 162.7, 161.1, 156.8, 148.8, 148.4, 144.6, 132.1, 128.7, 117.7, 115.0, 114.1, 112.6, 100.8, 56.8, 31.2; HRMS (ESI) Calculated for $C_{18}H_{13}N_3O_8Na$ [M+Na]⁺: 422.0589. Found: 422.0595. m.p.: 233° C.

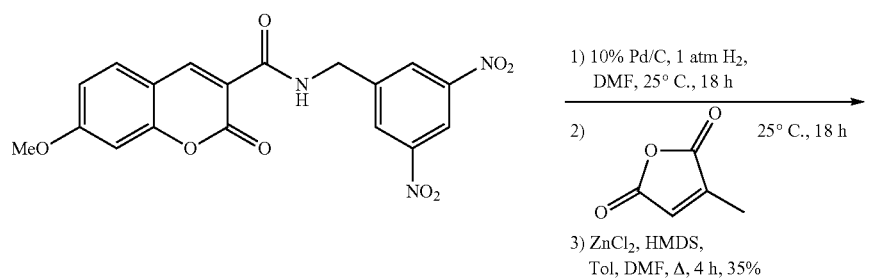

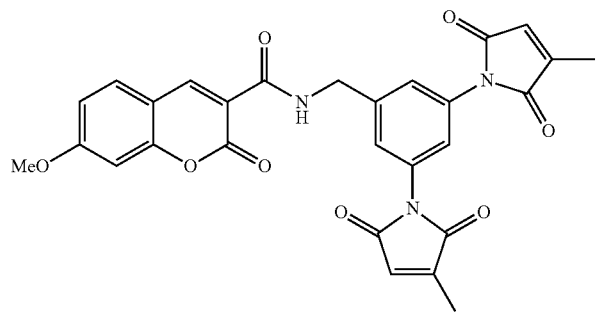

7-Methoxy-3-(3,5-di-(3-methylmaleimido)benzyl)aminocarbonyl coumarin (11): To a suspension of 9 (80 mg, 0.203 mmol) in DMF (8 mL) was added Pd/C 10% (50% H₂O w/w). The resulting mixture was stirred under hydrogen (1 atm) at 25° C. for 18 hours after which it was filtered on celite. The resulting diamine 10 was subsequently used in the next step without further purification.

Citraconic anhydride (0.06 mL, 0.609 mmol) was added to the filtrate and the resulting mixture was stirred at 25° C. for 18 hours after which toluene (20 mL) was added, followed by ZnCl₂ (83 mg, 0.609 mmol) and HMDS (0.13 mL, 0.609 mmol). The resulting mixture was heated to reflux for 4 hours and solvents were evaporated under reduced pressure. The crude reaction mixture was dissolved in EtOAc and the organic phase was washed successively with 0.1 M HCl and saturated Na₂CO₃, dried over MgSO₄ and evaporated under reduced pressure to give the title compound 11 as a beige solid (38 mg, 0.072 mmol, 35%). ¹H NMR (400 MHz, DMSO-d₆) δ 9.20 (bs, 1NH), 8.86 (s, 1H), 7.95-7.91 (m, 2H), 7.35 (s, 1H), 7.22 (s, 1H), 7.13 (s, 1H), 7.05 (d, J=8.0 Hz, 1H), 6.81 (s, 2H), 4.61 (d, J=5.2 Hz, 2H), 3.91 (s, 3H), 2.07 (s, 6H); ¹³C NMR (75 MHz, DMSO-d₆) δ 171.6, 170.7, 165.8, 163.0, 162.0, 157.5, 149.4, 147.1, 142.3, 133.6, 132.9, 128.8, 126.0, 124.6, 1156.0, 115.0, 113.4, 101.6, 57.5, 43.5, 12.1; HRMS (ESI) Calculated for C₂₈H₂₂N₃O₈ [M+H]⁺: 528.1421. Found: 528.1401.

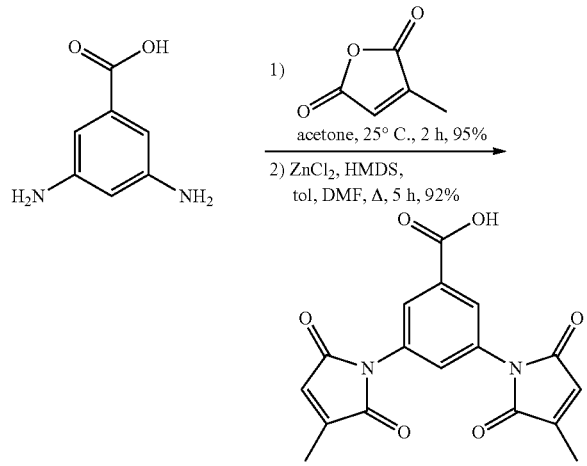

3,5-Di-(3-methylmaleimido)benzoic acid (12): To a solution of 3,5-diaminobenzoic acid (1.0 g, 6.58 mmol) in acetone (40 mL) was added citraconic anhydride (1.8 mL, 19.74 mmol) and the resulting mixture was stirred at 25° C. for 2 hours after which solvents were evaporated under reduced pressure. The crude solid was triturated in Et₂O, filtered under reduced pressure and used in the next step without further purification. The dimaleamic acid (500 mg, 1.33 mmol) was dissolved in DMF (5 mL) and then toluene (40 mL) was added, followed by ZnCl₂ (544 mg, 3.99 mmol) and HMDS (1.13 mL, 5.98 mmol). The resulting mixture was heated to reflux for 5 hours after which the solvents were evaporated. The title compound 12 was obtained as an off-white solid after precipitation with 0.1 M HCl (417 mg, 1.22 mmol, 92%). ¹H NMR (300 MHz, DMSO-d₆) δ 7.94 (d, J=1.8 Hz, 2H), 7.62 (t, J=1.8 Hz, 1H), 6.83 (q, J=1.8 Hz, 2H), 2.08 (d, J=1.8 Hz, 6H); ¹³C NMR (75 MHz, DMSO-d₆) δ 170.4, 169.5, 166.2, 146.2, 132.8, 132.2, 128.2, 127.8, 126.0, 11.0; HRMS (ESI) Calculated for C₁₇H₁₃N₂O₆ [M+H]⁺: 341.0768. Found: 341.0770. m.p.: 254° C. (dec.).

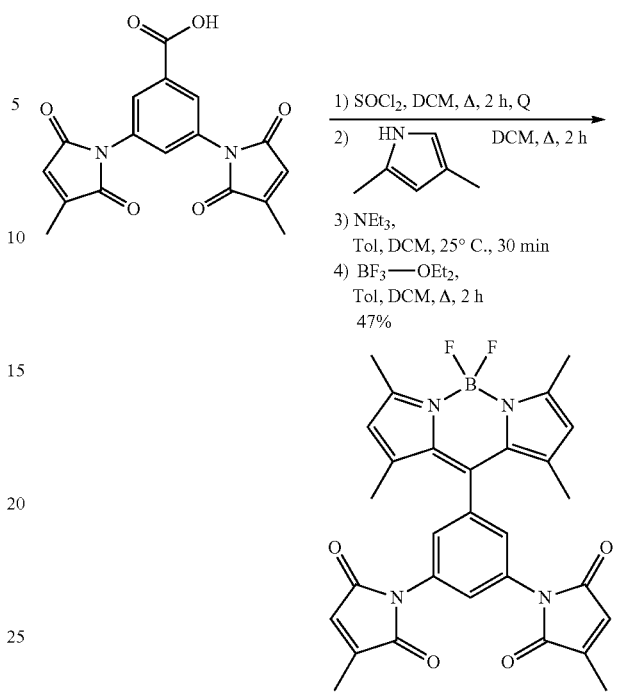

8-(3',5'-di-(3-methylmaleimido)-phenyl-4,4-difluoro-4-bora-3a,4a-diaza-s-indacene (13; BODIPY): Acid 12 (80 mg, 0.235 mmol) in DCM (15 mL) was treated with thionyl chloride (3 mL) and heated to reflux for 2 hours after which the volatiles were evaporated. The crude mixture was dissolved in CHCl₃ and evaporated again 3 more times and the resulting acid chloride was used in the next step without further purification. 1,3-Dimethylpyrrole was added to a solution of the acid chloride in DCM (20 mL). The resulting mixture was stirred at 50° C. for 2 hours after which the volatiles were evaporated. The resulting solid was dissolved in DCM/Tol (5/20 mL) and then treated with NEt₃ (0.20 mL, 1.41 mmol) at 25° C. for 30 minutes, followed by the addition of BF₃.OEt₂ (0.06 mL, 0.470 mmol). The resulting mixture was heated at 70° C. for 2 hours. Solvents were evaporated and the crude was purified by flash chromatography on silica gel DCM/THF giving a dark pink solid (60 mg, 0.111 mmol, 47%). ¹H NMR (400 MHz, CDCl₃) δ 7.66 (bs, 2H), 7.35 (bs, 1H), 6.48 (bs, 2H), 5.98 (s (1), 1H), 5.87 (s (1), 1H), 2.53 (s, 6H), 2.28 (s, 6H), 1.55 (s, 6H); ¹³C NMR (75 MHz, CDCl₃) δ 183.5, 170.8, 169.7, 156.9, 146.9, 144.3, 142.1, 137.1, 134.1, 133.2, 132.0, 128.5, 124.8, 124.7, 124.6, 122.4, 114.1, 15.5, 14.8, 12.0; HRMS (ESI) Calculated for C₂₉H₂₆BF₂N₄O₄ [M+H]⁺: 543.2031. Found: 543.2010. m.p.: 118° C.

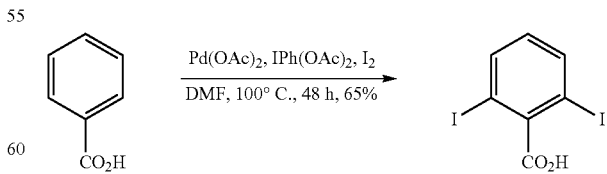

2,6-Diiodobenzoic acid (14): Benzoic acid (500 mg, 4.54 mmol), Pd(OAc)₂ (52 mg, 0.23 mmol), IPh(O₂CF₃)₂ (2.19 g, 6.81 mmol) and iodine (1.73 g, 6.81 mmol) were dissolved in DMF (10 mL) in a screw cap tube and the resulting mixture was heated at 100° C. over 48 hours. The mixture was cooled to 25° C., EtOAc was added and the organic phase was washed with 0.5 M HCl and saturated aqueous NaCl. The crude mixture was then purified by flash chromatography on silica gel (60% DCM/40% hexanes) to give 14 as a white solid (1.10 g, 2.95 mmol, 65%). Characterization was consistent as published (*Angew. Chem. Int Ed.* 2008, 47, 5215-5219).

2,6-Bis((4-tert-butoxycarbonylaminophenyl)ethynyl)benzoic acid (15): In a two-neck flask equipped with a condenser and a stirring bar were placed $PdCl_2(PPh_3)_2$ (38 mg, 0.054 mmol), CuI (5 mg, 0.027 mmol) and 14 (1.0 g, 2.68 mmol). The system was purged with a 1/1 mixture of $N_2/H_2$. Solids were then suspended in previously degassed $NEt_3$ (2.2 mL, 16.1 mmol), then heated to 80° C. after which a 4-N-Boc-ethynylaniline solution (1.2 mg, 5.36 mmol) in ACN (20 mL) was added. The resulting mixture was heated to reflux over 18 hours after which it was filtered on a celite pad and solvents were removed by evaporation. The crude product was purified by flash chromatography on silica gel (DCM/30% Tol to DCM/10% Tol gradient) to give 15 as a yellow solid (930 mg, 1.68 mmol, 61%). $^1$H NMR (400 MHz, $CDCl_3$) δ 7.77-7.73 (m, 2H), 7.59-7.54 (m, 4H), 7.52-7.50 (m, 1H), 7.45-7.41 (m, 4H), 6.30 (bs, 2 NH), 1.56 (bs, 18H); HRMS (ESI) Calculated for $C_{33}H_{33}N_2O_6$ [M+H]$^+$: 553.2339. Found: 553.2333. m.p. 118° C.

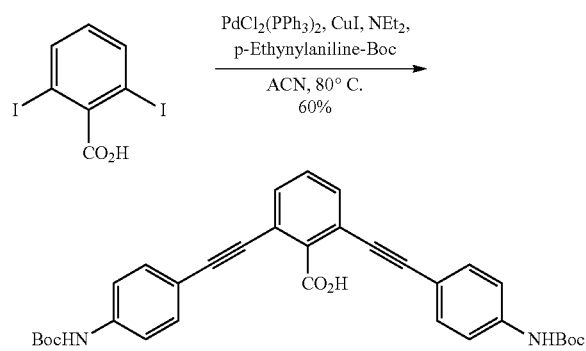

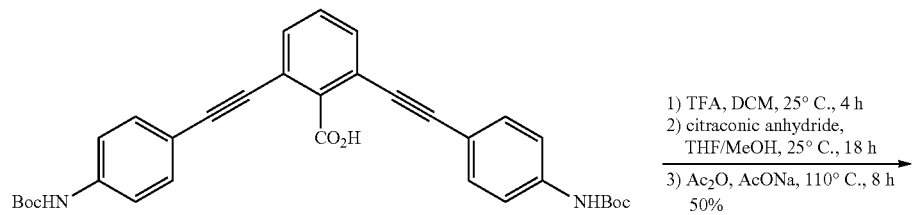

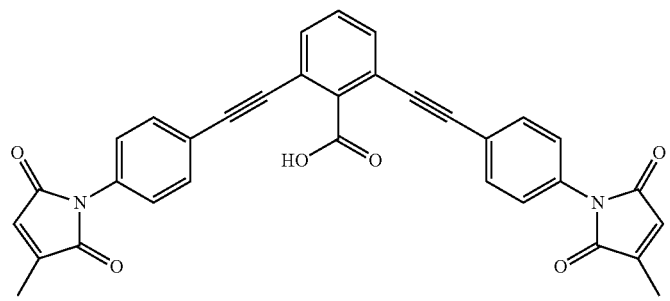

2,6-Bis((4-(3-methylmaleimido)phenyl)ethynyl)benzoic acid (16): TFA (2.85 mL, 37 mmol) was added to a solution of 15 (508 mg, 0.920 mmol) in DCM (25 mL) and the resulting mixture was stirred at 25° C. over 3 hours after which solvents were evaporated under reduced pressure. The resulting dianiline intermediate was used in the next step without further purification.

The dianiline was dissolved in THF/MeOH (15/5 mL) and then treated with citraconic anhydride (0.25 mL, 2.76 mmol) at 25° C. over 18 hours after which solvents were evaporated under reduced pressure. The resulting dimaleamic acid was dissolved in Ac$_2$O and treated with NaOAc (30 mg, 0.368 mmol) at 110° C. over 8 hours after which solvents were evaporated. The resulting oil was dissolved in DCM and the organic phase was washed with 0.1 M HCl, dried over MgSO$_4$ and evaporated under reduced pressure. The dimaleimide 16 was precipitated as a yellow solid upon addition of Et$_2$O and Hexanes (255 mg, 0.472 mmol, 51%). $^1$H NMR (400 MHz, CDCl$_3$) δ 7.96-7.87 (m, 3H), 7.77-7.68 (m, 4H), 7.49-7.45 (m, 4H), 6.51 (bs, 2H), 2.19 (bs, 6H); HRMS (ESI) Calculated for C$_{33}$H$_{21}$N$_2$O$_6$ [M+H]$^+$: 541.1397. Found: 541.1394.

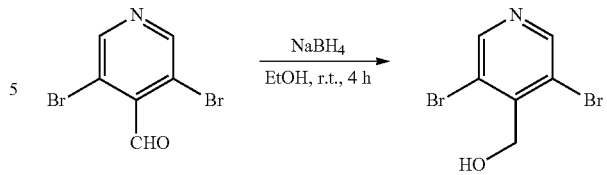

(3,5-dibromopyridin-4-yl)methanol (18): Solid NaBH$_4$ (35 mg, 0.91, mmol) was added to a solution of 3,5-dinitrobenzoic acid (220 mg, 0.83 mmol) in absolute ethanol (10 mL) at 0° C. The resulting mixture was warmed to 25° C. and stirred for 4 hours after which the reaction was quenched with aqueous NH$_4$Cl. The aqueous phase was extracted with EtOAc and the organic phase was dried over MgSO$_4$ and evaporated under reduced pressure to give the title compound as a white solid (212 mg, 0.80 mmol, 96%). $^1$H NMR (300 MHz, (CDCl$_3$) δ 8.67-8.63 (m, 2H), 4.96 (bs, 2H), 2.69 (bs, OH).

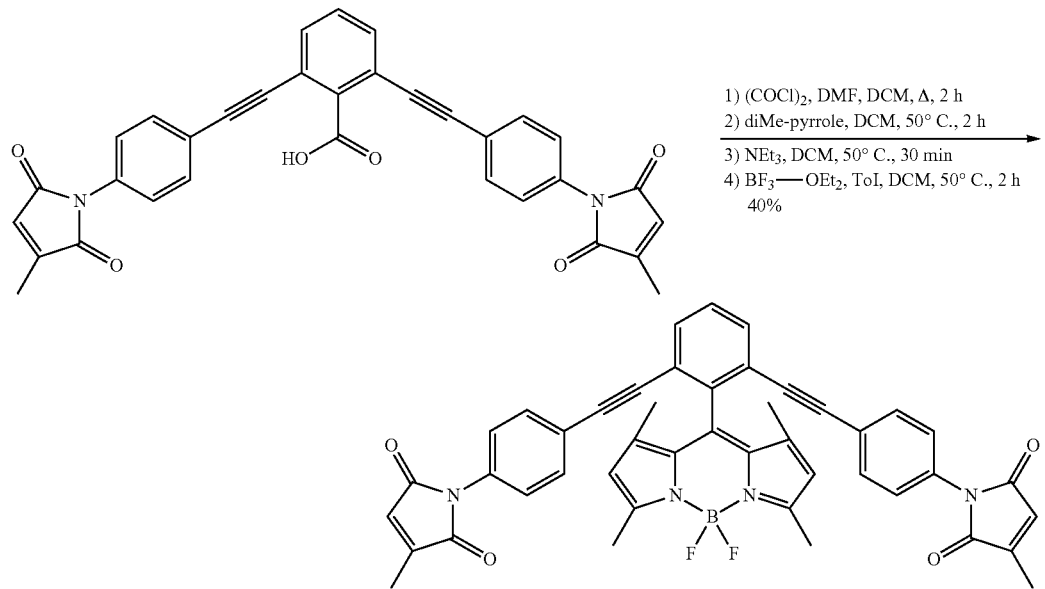

8-(2',6'-di-((4''-(3-methylmaleimido)phenyl)ethynyl))-4,4-difluoro-4-bora-3a,4a-diaza-s-indacene (17): A solution of 16 (75 mg, 0.139 mmol) in DCM (7 mL) was treated with oxalyl chloride (18 μL, 0.208 mmol) and one drop of DMF at 60° C. over 2 hours after which solvents were evaporated under reduced pressure. The resulting acyl chloride was dissolved in DCM which was subsequently evaporated (repeated three times), and then used in the next step without further purification.

To a solution of the acyl chloride in DCM (3 mL) was added 2,4-dimethylpyrrole (29 μL, 0.278 mmol) and the resulting mixture was stirred at 50° C. over 2 hours after which toluene (3 mL) and Et$_3$N were added. The resulting mixture was stirred at 50° C. for 30 minutes before BF$_3$—OEt$_2$ (0.47 mL, 1.95 mmol) was added and the solution was heated at 50° C. over 90 minutes. The solvents were then evaporated under reduced pressure and the crude product was purified by flash chromatography (DCM/Hex) to give 17 as a red solid (45 mg, 0.061 mmol, 44%).

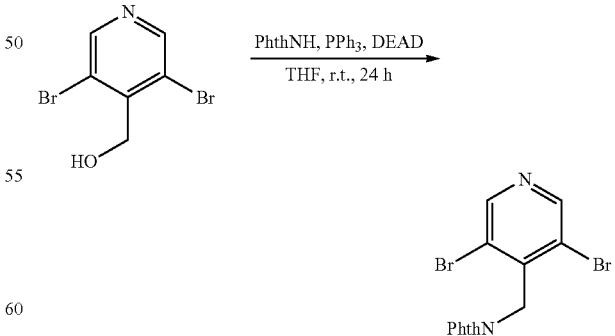

N-(3,5-dibromopyridin-4-yl)methylphthalimide (19): To a solution of benzylic alcohol 18 (300 mg, 1.13 mmol), triphenylphosphine (357 mg, 1.36 mmol) and phthalimide (200 mg, 1.36 mmol) in dry THF (10 mL) was added DIAD (0.26 mL, 1.36 mmol) under an N$_2$ atmosphere. The resulting mixture was stirred at 25° C. for 24 hours after which solvents were evaporated under reduced pressure. The crude product mixture was purified by chromatography on silica gel to give the title compound 19 as a white (300 mg, 0.762 mmol, 67%). $^1$H NMR (400 MHz, CDCl$_3$) δ 8.68 (bs, 2H), 7.88-7.83 (m, 2H), 7.78-7.75 (m, 2H), 5.13 (s, 2H); $^{13}$C NMR (75 MHz, CDCl$_3$) δ 168.1, 151.8, 142.7, 135.1, 132.4, 124.4, 43.3; MS (ESI) Calculated for C$_{14}$H$_9$N$_2$O$_2$Br$_2$ [M+H]$^+$: 397.04. Found: 396.90.

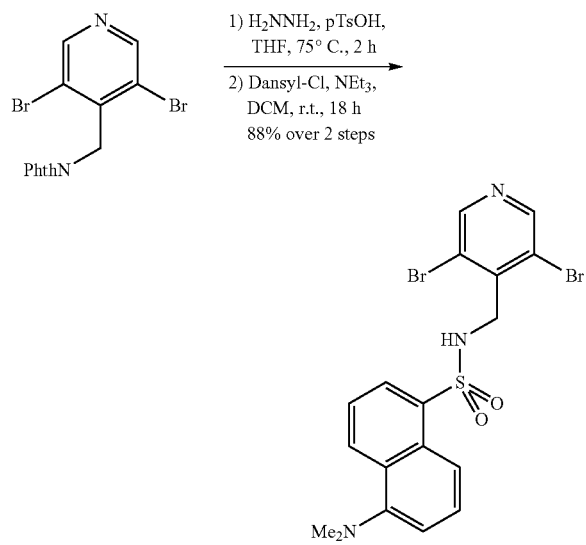

N-(3,5-dibromopyridin-4-yl)methylphthalimide (20): To a solution of phthalimide 19 (300 mg, 0.76 mmol) in THF (10 mL) were added hydrazine (0.30 mL, 6.10 mmol) and a catalytic amount of p-toluenesulfonic acid (4 mg, 0.15 mmol). The resulting mixture was heated to reflux over 90 minutes after which saturated aqueous Na$_2$CO$_3$ was added. The aqueous phase was extracted with EtOAc and the organic phases were combined, dried over MgSO$_4$ and evaporated under reduced pressure. The resulting benzylic amine was used in the next step without further purification.

The benzylic amine was dissolved in DCM (15 mL) and then added to a solution of dansyl chloride (246 mg, 0.91 mmol) and Et$_3$N (0.21 mL, 1.52 mmol). The resulting mixture was stirred at 25° C. overnight after which solvents were evaporated under reduced pressure. The crude reaction mixture was purified by chromatography on silica gel to give the title compound as a pale green solid (332 mg, 0.668 mmol, 88%). $^1$H NMR (300 MHz, CDCl$_3$) δ 8.42 (d, J=8.7 Hz, 1H), 8.30 (d, J=8.7 Hz, 1H), 8.17 (bs, 1H), 8.14 (s, 2H), 7.49 (t, J=8.7 Hz, 1H), 7.42 (t, J=8.7 Hz, 1H), 7.12 (d, J=8.7 Hz, 1H), 5.90 (t, J=6.6 Hz, NH), 4.42 (d, J=6.9 Hz), 2.85 (s, 6H); $^{13}$C NMR (75 MHz, CDCl$_3$) δ 152.7, 151.1, 143.5, 134.6, 131.6, 131.3, 130.1, 130.0, 129.5, 123.8, 123.5, 119.5, 116.0, 47.0, 46.2.

REFERENCES

1. Liang, F.; Holt, I.; Pertea, G.; Karamycheva, S.; Salzberg, S.; Quackenbush, J.: "Gene index analysis of the human genome estimates approximately 120,000" Nat. Genet. 2000, 25, 239-240.
2. Roest Crollius, H.; Jaillon, O.; Dasilva, C.; Bouneau, L.; Fischer, C.; Fizames, C.; Wincker, P.; Brottier, P.; Quetier, F.; Saurin, W.; Weissenbach, J.: "Estimate of human gene number provided by genome-wide analysis using", Nat. Genet. 2000, 25, 235-238.
3. Ewing, B.; Green, P.: "Analysis of expressed sequence tags indicates 35,000 human genes", Nat. Genet. 2000, 25, 232-234.
4. For example, see Haughland, R. P. In Handbook of Fluorescent Probes and Research Chemicals, Molecular Probes, Eugene, Oreg., 1992, 5th Edn.
5. Sipple, T. O.: "New fluorochromes for thiols: maleimide and iodoacetamide derivatives of 3-phenyl coumarin fluorophore", J. Histochem. Cytochem. 1981, 29, 314-321.
6. Corrie, J. E. T.: "Thiol-reactive Fluorescent Probes for Protein Labeling", J. Chem. Soc. Perkin Trans. 1 1994, 2975-2982.
7. For a recent review, see: Zhang, J.; Campbell, R. E.; Ting, A. Y.; Tsien, R. Y.: "Creating New Fluorescent Probes for Cell Biology", Nature Rev. 2002, 3, 906-918.
8. Tsien, R. Y.: "The Green Fluorescent Protein", Annu. Rev. Biochem. 1998, 67, 509-544.
9. Griffin, B. A.; Adams, R. S.; Tsien, R. Y.: "Specific Covalent Labeling of Recombinant Protein Molecules Inside Live Cells", Science 1998, 281, 269-272.
10. Griffin, B. A.; Adams, S. R.; Jones, J.; Tsien, R. Y.: "Fluorescent labeling of recombinant proteins in living cells with FlAsH", Methods Enzymol. 2000, 327, 565-578.
11. Gaietta, G.; Deerinck, T. J.; Adams, S. R.; Bouwer, J.; Tour, O.; Laird, D. W.; Sosinsky, G. E.; Tsien, R. Y.; Ellisman, M. H.: "Multicolor and Electron Microscopic Imaging of Connexin Trafficking", Science 2002, 296, 503-507.
12. Girouard, S.; Keillor, J. W. "Elaboration d'un fluorophore permettant une étude d'apposition protéique", M. Sc. Thesis, Université de Montréal, 2000.
13. Houle, M.-H.; Keillor, J. W. "Synthèse d'un composé fluorogénique permettant l'étude de l'apposition protéique", M. Sc. Thesis, Université de Montréal, 2003.
14. Kanaoka, Y.; Sekine, T.; Machida, M.; Soma, Y.; Tanizawa, K.; Ban, Y.: "Studies on Protein-Sulfuryl Reagent. Synthesis of Benzimidazole Derivatives of Maleimide; Fluorescent Labeling of Maleimide", Chem. Pharm. Bull. 1964, 12, 127.
15. Guy, J.; Caron, K.; Dufresne, S.; Michnick, S. W.; Skene, W.; Keillor, J. W.: "Convergent Preparation and Photophysical Characterization of Dimaleimide Dansyl Fluorogens: Elucidation of the Maleimide Fluorescence Quenching Mechanism", J. Am. Chem. Soc. 2007, 129, 11969.
16. Langmuir, M. E.; Yang, J. R.; Moussa, A. M.; Laura, R.; LeCompte, K. A.: "New Naphtopyranone Based Fluorescent Thiol Probes", Tetrahedron Lett. 1995, 36, 3989.
17. Yang, J.-R.; Langmuir, M. E.: "Synthesis and Properties of a Maleimide Fluorescent Thiol Reagent Derived a Naphtopyranone", J. Heterocyclic Chem. 1991, 28, 1177.
18. U.S. Pat. No. 7,700,375.
19. Russ, A.; Bump, E. A.: "Detection and quantitation of biological sulfhydryls", Methods Biochem. Anal. 1988, 33, 165-241.

What is claimed is:

1. A fluorescent marker of Formula I:

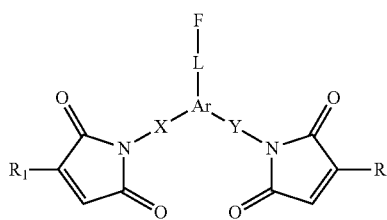

Formula I wherein:
i) X and Y are

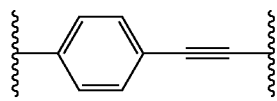

ii) R and $R_1$ are independently selected from H and alkyl;
iii) Ar is phenyl or pyridyl;
iv) L is a spacer selected from the group consisting of —NH—; —$(CH_2)_n$NH—; —$NHSO_2$—; —$(CH_2)_n$NHCO—; -(cycloalkyl)NHCO—; —$(CH_2)_n$$NHSO_2$—; -(cycloalkyl)$NHSO_2$—; —$CONH(CH_2)_n$NHCO—; —CONH(cycloalkyl)NHCO—; —NHCO$(CH_2)_n$NHCO—; —NHCO(cycloalkyl)NHCO—; —$(CH_2)_n$$SO_2$NH—; -(cycloalkyl)$SO_2$NH—; —$(CH_2)_n$NHCSNH—; -(cycloalkyl)NHCSNH—; —CR=$CR_1$—; —C≡C—; —$(CH_2)_n$N=CH—; -(cycloalkyl)N=CH—; —N=CH($CH_2$)—; —N=CH(cycloalkyl)-;

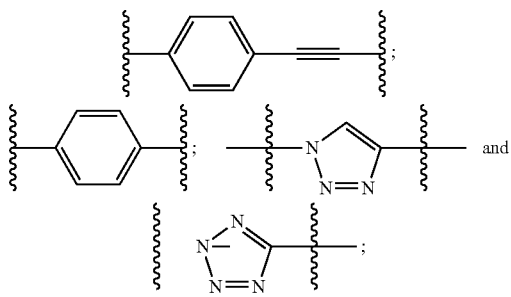

v) n is an integer ranging from 1 to 5;
vi) F is a fluorophore selected from the group consisting of fluorescein, rhodamine, eosin, thionine, safranin, coumarin, methoxycoumarin, dansyl, BODIPY and BODIPY derivatives; and wherein X, Y and L may be independently positioned in a 1,3,5; 1,2,3; 1,3,4 or in a 3,4,5 configuration.

2. The fluorescent marker of claim 1, wherein said marker comprises a compound of Formula Ia:

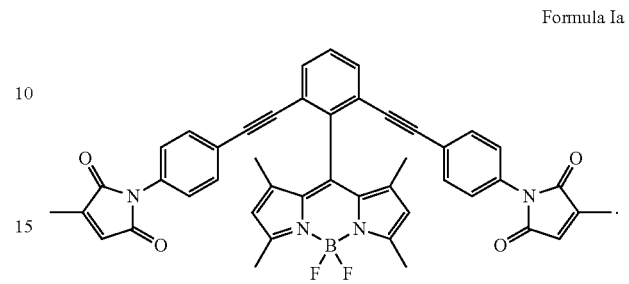

Formula Ia

3. The fluorescent marker of claim 1, wherein said marker comprises a compound of Formula Ie:

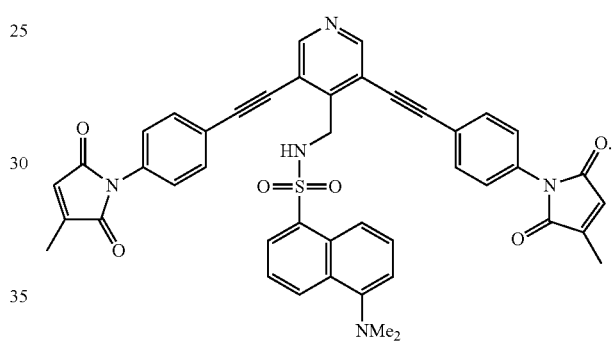

Formula Ie

4. A kit for assaying target proteins having sterically unhindered sulfhydryl groups, the kit comprising a fluorescent marker as claimed in claim 1.

5. The kit of claim 4, further comprising instructions for use.

6. A kit for assaying biomolecular interactions between a first interacting protein and a second interacting protein, wherein the first interacting protein is linked or fused to a first target protein having sterically unhindered sulfhydryl groups, and the second interacting protein is linked or fused to a second target protein having sterically unhindered sulfhydryl groups, the kit comprising at least two fluorescent markers as claimed in claim 1.

7. The kit of claim 6, further comprising instructions for use.

* * * * *